United States Patent
Tan et al.

(10) Patent No.: US 7,208,282 B2
(45) Date of Patent: Apr. 24, 2007

(54) RHESUS MONKEY, DOG AND FERRET MELANIN-CONCENTRATING HORMONE TYPE 2 RECEPTOR

(75) Inventors: Carina Tan, Metuchen, NJ (US); Hideki Sano, Nagareyama (JP)

(73) Assignees: Merck & Co., Inc., Rahway, NJ (US); Banyu Pharmaceutical Co., Ltd., Chuo-ku, Tokyo (JP)

(*) Notice: Subject to any disclaimer, the term of this patent is extended or adjusted under 35 U.S.C. 154(b) by 170 days.

(21) Appl. No.: 10/478,534

(22) PCT Filed: May 28, 2002

(86) PCT No.: PCT/US02/16702

§ 371 (c)(1),
(2), (4) Date: Nov. 20, 2003

(87) PCT Pub. No.: WO02/097394

PCT Pub. Date: Dec. 5, 2002

(65) Prior Publication Data

US 2004/0132045 A1    Jul. 8, 2004

Related U.S. Application Data

(60) Provisional application No. 60/294,747, filed on May 31, 2001.

(51) Int. Cl.
  C07K 14/705    (2006.01)
  C12N 15/12    (2006.01)
  G01N 33/566    (2006.01)
(52) U.S. Cl. ................ 435/7.21; 435/69.1; 435/252.3; 435/320.1; 530/350; 536/23.5
(58) Field of Classification Search .............. None
See application file for complete search history.

(56) References Cited

U.S. PATENT DOCUMENTS

| | | | |
|---|---|---|---|
| 5,264,565 A | 11/1993 | England et al. |
| 5,480,784 A | 1/1996 | Kacian et al. |
| 5,686,597 A | 11/1997 | Coleman et al. |
| 5,852,188 A | 12/1998 | Cook |
| 5,859,221 A | 1/1999 | Cook et al. |
| 6,033,872 A | 3/2000 | Bergsma et al. |
| 6,221,613 B1 | 4/2001 | Salon et al. |
| 6,362,326 B1 | 3/2002 | Sathe et al. |
| 6,593,108 B1 | 7/2003 | Liu et al. |
| 2003/0114644 A1 | 6/2003 | Kinrade et al. |
| 2003/0166834 A1 | 9/2003 | Kinrade et al. |

FOREIGN PATENT DOCUMENTS

| | | |
|---|---|---|
| EP | 1 033 401 | 2/2000 |
| WO | WO 94/01548 | 1/1994 |
| WO | WO 96/18651 | 6/1996 |
| WO | WO 97/05252 | 2/1997 |
| WO | WO 98/02582 | 1/1998 |
| WO | WO 99/28492 | 6/1999 |
| WO | WO 00/37113 | 6/2000 |
| WO | WO 00/49046 | 8/2000 |
| WO | WO 00/75166 | 12/2000 |
| WO | WO 01/05947 | 1/2001 |
| WO | WO 01/07606 | 2/2001 |
| WO | WO 01/07611 | 2/2001 |
| WO | WO 01/36471 | 5/2001 |
| WO | WO 01/62797 | 8/2001 |
| WO | WO 01/70975 | 9/2001 |
| WO | WO 02/08290 | 1/2002 |

OTHER PUBLICATIONS

An, S. et al. "Identification and characterization of a melanin-concentrating hormone receptor", Proc. Natl. Acad. Sci USA, 2001, vol. 98, pp. 7576-7581.

Bachner, D. et al. "Identification of melanin concentrating hormone (MCH) as the natural ligand for the orphan somatostatin-like receptor 1 (SLC-1)", FEBS Letters, 1999, vol. 457, pp. 522-524.

Bednarek, M. et al. "Short Segment of Human Melanin-Concentrating Hormone That Is Sufficient for Full Activation of Human Melanin-Concentrating Hormone Receptors 1 and 2", Biochemistry, 2001, vol. 40, pp. 9379-9386.

Bork, P. et al. "Go hunting in sequence databases but watch out for traps", Trends in Genetics, 1996, vol. 12, pp. 425-427.

Bork, P. "Powers and Pitfalls in Sequence Analysis: The 70% Hurdle", Genome Research, 2000, vol. 10, pp. 398-400.

Brenner, S. "Errors in genome annotation", Trends in Genetics, 1999, vol. 15, pp. 132-133.

Breton, C. et al. "Isolation and characterization of the human melanin-concentrating hormone gene and a variant gene", Molecular Brain Research, 1993, vol. 18, pp. 297-310.

Chambers, J. et al. "Melanin-concentrating hormone is the cognate ligand for the orphan G-protein-coupled receptor SLC-1", Nature, 1999, vol. 400, pp. 261-265.

Doerks, T. et al. "Protein annotation: detective work for function prediction", Trends in Genetics, 1998, vol. 14, pp. 248-250.

Erickson, J. et al., "Sensitivity to leptin and susceptibility to seizures of mice lacking neuropeptide Y", Nature, 1996, vol. 381, pp. 415-418.

(Continued)

Primary Examiner—John Ulm
(74) Attorney, Agent, or Firm—Sheldon O. Heber

(57) ABSTRACT

The present invention identifies the presence of MCH-2R in the dog, ferret and rhesus monkey. MCH-2R is a G-protein coupled receptor that responds to MCH and is distinct from MCH-1R. MCH-2R polypeptide and nucleic acid sequences related to the dog, ferret, and rhesus monkey MCH-2R are described herein along with uses of such polypeptides and nucleic acids.

18 Claims, 6 Drawing Sheets

OTHER PUBLICATIONS

Flier, J. et al. "Obesity and the Hypothalamus: Novel Peptides for New Pathways", Cell, 1998, vol. 92, pp. 437-440.

Hill, J. et al. "Molecular Cloning and Functional Characterization of MCH2, a Novel Human MCH Receptor", The Journal of Biological Chemistry, 2001, vol. 276, pp. 20125-20129.

Knigge, K. et al. "Melanotropic Peptides in the Mammalian Brain: The Melanin-Concentrating Hormone", Peptides, 1996, vol. 17, pp. 1063-1073.

Lakaye, B. et al. "Cloning of the rat brain cDNA encoding for the SLC-1 G protein-coupled receptor reveals the presence of an intron in the gene", Biochimica et Biophysica Acta, 1998, vol. 1401, pp. 216-220.

Lembo, P. et al. "The receptor for the orexigenic peptide melanin-concentrating hormone is a G-protein-coupled receptor", Nature Cell Biology, 1999, vol. 1, pp. 267-271.

Ludwig, D. et al. "Melanin-concentrating hormone overexpression in transgenic mice leads to obesity and insulin resistance", The Journal of Clinical Investment, 2001, vol. 107, pp. 379-386.

Mahairas, G. et al., "Sequence-tagged connectors: A sequence approach to mapping and scanning the human genome", Proc. Natl. Acad. Sci. USA, 1999, vol. 96, pp. 9739-9744.

Mori, M. et al. "Cloning of a Novel G Protein-Coupled Receptor, SLT, a Subtype of the Melanin-Concentrating Hormone Receptor", Biochemical and Biophysical Research Communications, 2001, vol. 283, pp. 1013-1018.

Nahon, J. "The Melanin-Concentrating Hormone: From the Peptide to the Gene", Critical Reviews in Neurobiology, 1994, vol. 8, pp. 221-262.

Ngo, J. et al. "Computational Complexity, Protein Structure Prediction, and the Levinthal Paradox" in *The Protein Folding Problem and Tertiary Structure Prediction*, edited by K. Merz and S. L. Grand, Chapter 14, pp. 492-495, Birkhäuser, Boston (1994).

Pearson, W. "Rapid and Sensitive Sequence Comparison with FASTP and FASTA", Methods in Enzymology, 1990, vol. 183, pp. 63-98.

Qu, D. et al. "A role for melanin-concentrating hormone in the central regulation of feeding behaviour", Nature, 1996, vol. 380, pp. 243-247.

Rodriguez, M. et al. "Cloning and Molecular Characterization of the Novel Human Melanin-Concentrating Hormone Receptor MCH2", Molecular Pharmacology, 2001, vol. 60, pp. 632-639.

Sailer, A. et al. "Identification and characterization of a second melanin-concentrating hormone receptor, MCH-2R", Proc. Natl. Acad. Sci. USA, 2001, vol. 98, pp. 7564-7569.

Saito, Y. et al. "Molecular characterization of the melanin-concentrating-hormone receptor", Nature, 1999, vol. 400, pp. 265-269.

Shimada, M. et al. "Mice lacking melanin-concentrating hormone are hypophagic and lean", Nature, 1998, vol. 396, pp. 670-674.

Shimomura, Y. et al. "Isolation and Identification of Melanin-Concentrating Hormone as the Endogenous Ligand of the SLC-1 Receptor", Biochemical and Biophysical Research Communications, 1999, vol. 261, pp. 622-626.

Skolnick, J. et al. "From genes to protein structure and function: novel applications of computational approaches in the genomic era", Trends in Biotechnology, 2000, vol. 18, pp. 34-39.

Smith, T. et al. The challenges of genome sequence annotation or "The devil is in details", Nature Biotechnology, 1997, vol. 15, pp. 1222-1223.

Tan, C. et al. "Melanin-Concentrating Hormone Receptor Subtypes 1 and 2: Species-Specific Gene Expression", Genomics, 2002, vol. 79, pp. 785-792.

Wells, J. et al. "Addititivy of Mutational Effects in Proteins", Biochemistry, 1990, vol. 29, pp. 8509-8517.

Database WPI, Section Ch, Week 200173, Derwent Publications Ltd., London, GB; AN 2001-639126 & WO 01/70975 A (Yamanouchi Pharmaceutical Company, Ltd.), Sep. 27, 2001.

Database WPI, Section Ch, Week 200049, Derwent Publications Ltd., London, GB; AN 2000-543749, & WO 01/49046 A (Takeda Chemical Industries, Ltd.), Aug. 24, 2000.

Geneseq Entry Concerning EP 1 033 401 A2, Oct. 6, 2000.

GenBank Accession No. H04706, Jun. 20, 1995.

GenBank Accession No. AQ190629, Nov. 4, 1998.

GenBank Accession No. AQ747249, Juy 19, 1999.

|  | 1 | | | | 50 |
|---|---|---|---|---|---|
| dogMCH2Rpep | MYSLHSSCWN | TSAEPLNKSC | NKEFAYHTLS | ILDTIRLPSM | IGIICSMGLV |
| ferretMCH2Rpep | MNPFHASCWN | TSAELLNKSC | NKESAYQTLR | IVDTIILPSM | IGIICSMGLV |
| humanMCH2Rpep | MNPFHASCWN | TSAELLNKSW | NKEFAYQTAS | VVDTVILPSM | IGIICSTGLV |
| rhesusMCH2Rpep | MNPFHSSCWN | TSAELSNKSW | NKEFAYQTAS | VVDTVILPSM | IGIICSTGLV |

|  | 51 | | | | 100 |
|---|---|---|---|---|---|
| dogMCH2Rpep | GNILIVFTII | RSRKKTIPDI | YICNLAVADL | VHIIGMPFLI | HQWARGGEWV |
| ferretMCH2Rpep | GNVLIVFTII | RSRKKTIPDI | YICNLAVADL | VHIIGMPFLI | HQWARGGEWV |
| humanMCH2Rpep | GNILIVFTII | RSRKKTVPDI | YICNLAVADL | VHIVGMPFLI | HQWARGGEWV |
| rhesusMCH2Rpep | GNILIVFTII | RSRKKTVPDI | YICNLAVADL | VHIIGMPFLI | HQWARGGEWV |

|  | 101 | | | | 150 |
|---|---|---|---|---|---|
| dogMCH2Rpep | FGGPLCTIIT | SLDTCNQFAC | SAIMTVMSID | RYLALVQPFR | LTSWRTRYKT |
| ferretMCH2Rpep | FGGPLCTIIT | SLDTCNQFAC | SAIMTVMSVD | RYLALVQPFR | LTSWRTRYKT |
| humanMCH2Rpep | FGGPLCTIIT | SLDTCNQFAC | SAIMTVMSVD | RYFALVQPFR | LTRWRTRYKT |
| rhesusMCH2Rpep | FGGPLCTIIT | SLDTCNQFAC | SAIMTVMSVD | RYFALVQPFR | LTSWRTRYKT |

|  | 151 | | | | 200 |
|---|---|---|---|---|---|
| dogMCH2Rpep | IRINLGLWAA | SFILALPVWV | YSKVIKFKDG | VESCAFDLTS | PDDVLRYTLY |
| ferretMCH2Rpep | IRINLGLWAA | SFILALPVWV | YSKVIKFKDG | VESCAFDLTS | PDDVLRYTLY |
| humanMCH2Rpep | IRINLGLWAA | SFILALPVWV | YSKVIKFKDG | VESCAFDLTS | PDDVLWYTLY |
| rhesusMCH2Rpep | IRINLGLWAA | SFVLALPVWI | YSKVIKFKDG | VESCAFDLTS | PDDVLWYTLY |

|  | 201 | | | | 250 |
|---|---|---|---|---|---|
| dogMCH2Rpep | LTITTFFFPL | PLILVCYILI | LCYTWEMYQQ | NKDARCYNPS | VPKERVMKLT |
| ferretMCH2Rpep | LTITTFFFPL | PLILVCYILI | LCYTWEMYQQ | NKDARCYNPS | VPKERVMKLT |
| humanMCH2Rpep | LTITTFFFPL | PLILVCYILI | LCYTWEMYQQ | NKDARCCNPS | VPKQRVMKLT |
| rhesusMCH2Rpep | LTITTFFFPL | PLILVCYILI | LCYTWEMYQQ | NKDARCCNPS | VPKQRVMKLT |

|  | 251 | | | | 300 |
|---|---|---|---|---|---|
| dogMCH2Rpep | KMVLVLVAVF | ILSAAPYHVI | QLVNLKMQQP | TLAFHVGYYL | SICFSYASSS |
| ferretMCH2Rpep | KMVLVLVAVF | ILSAAPYHVI | QLVNLQMEQP | TLAFHVGYYL | SICFSYASSS |
| humanMCH2Rpep | KMVLVLVVVF | ILSAAPYHVI | QLVNLQMEQP | TLAFYVGYYL | SICLSYASSS |
| rhesusMCH2Rpep | KMVLVLVAVF | ILSAAPYHVI | QLVNLQMEQP | TLAFYVGYYL | SICLSYASSS |

|  | 301 | | 341 | | |
|---|---|---|---|---|---|
| dogMCH2Rpep | INPFLYIMLS | GNFRKRLPQV | QRRVTEKSTI |  | (SEQ ID NO: 1) |
| ferretMCH2Rpep | INPFLYIMLS | GNFRKRLPQV | QRRVTEREIN | NMGNTLKSHF . | (SEQ ID NO: 2) |
| humanMCH2Rpep | INPFLYILLS | GNFQKRLPQI | QRRATEKEIN | NMGNTLKSHF . | (SEQ ID NO: 4) |
| rhesusMCH2Rpep | INPFLYILLS | GNFQKRLPQI | QRRVTDKEIK | NMGNTLKSHF . | (SEQ ID NO: 3) |

Fig. 1

```
                    1                                                      50
ferMCH2R    ATGAATCCAT TTCATGCATC TTGTTGGAAC ACCTCTGCTG AACTTTTAAA
huMCH2R     ATGAATCCAT TTCATGCATC TTGTTGGAAC ACCTCTGCTG AACTTTTAAA
dogMCH2R    ATGTATTCAC TTCACTCATC CTGTTGGAAC ACCTCTGCTG AACCTTTGAA
rhMCH2R     ATGAATCCAT TTCACTCATC TTGTTGGAAC ACCTCTGCCG AACTTTCAAA 51                                                     100
ferMCH2R    CAAATCCTGC AATAAAGAAT CTGCTTATCA AACCCTCAGA ATTGTGGATA
huMCH2R     CAAATCCTGC AATAAAGAAT CTGCTTATCA AACCCTCAGA ATTGTGGATA
dogMCH2R    CAAATCCTGC AATAAAGAGT TTGCTTATCA CACCCTCAGC ATTTTAGATA
rhMCH2R     CAAATCCTGG AATAAAGAGT TTGCTTATCA AACTGCCAGT GTTGTAGATA 101                                                    150
ferMCH2R    CAATCATCCT TCCTTCTATG ATTGGGATTA TCTGTTCAAT GGGGCTGGTT
huMCH2R     CAATCATCCT TCCTTCTATG ATTGGGATTA TCTGTTCAAT GGGGCTGGTT
dogMCH2R    CARTCAGGCT TCCTTCTATG ATTGGGATTA TCTGTTCAAT GGGGCTAGTT
rhMCH2R     CAGTCATCCT CCCTTCCATG ATTGGGATTA TCTGTTCAAC AGGGCTGGTT 151                                                    200
ferMCH2R    GGCAATGTCC TCATTGTATT CACTATAATA AGGTCCAGGA AAAAAACCAT
huMCH2R     GGCAATGTCC TCATTGTATT CACTATAATA AGGTCCAGGA AAAAAACCAT
dogMCH2R    GGCAACATCC TCATTGTATT CACTATAATA AGGTCCAGGA AAAAAACCAT
rhMCH2R     GGCAACATCC TCATTGTATT CACTATAATA AGGTCCAGAA AAAAAACAGT 201                                                    250
ferMCH2R    TCCTGACATT TATATCTGCA ACCTGGCTGT AGCTGATCTG GTTCACATCA
huMCH2R     TCCTGACATT TATATCTGCA ACCTGGCTGT AGCTGATCTG GTTCACATCA
dogMCH2R    TCCTGACATT TATATCTGCA ACCTGGCTGT GGCTGATCTG GTCCACATCA
rhMCH2R     CCCTGACATC TATATCTGCA ACCTGGCTGT GGCTGATTTG GTCCACATCA 251                                                    300
ferMCH2R    TTGGAATGCC TTTTCTTATT CATCAATGGG CCCGGGGAGG AGAGTGGGTG
huMCH2R     TTGGAATGCC TTTTCTTATT CATCAATGGG CCCGGGGAGG AGAGTGGGTG
dogMCH2R    TTGGAATGCC ATTTCTTATT CATCAGTGGG CCCGGGGAGG AGAGTGGGTG
rhMCH2R     TTGGAATGCC TTTTCTTATT CACCAGTGGG CCCGAGGGGG AGAGTGGGTA 301                                                    350
ferMCH2R    TTTGGGGGGC CCCTCTGCAC CATTATCACG TCGCTGGATA CCTGCAACCA
huMCH2R     TTTGGGGGGC CCCTCTGCAC CATTATCACG TCGCTGGATA CCTGCAACCA
dogMCH2R    TTTGGGGGGC CCCTCTGCAC CATTATCACA TCCCTGGATA CCTGCAACCA
rhMCH2R     TTTGGGGGGC CTCTCTGCAC CATCATCACA TCCCTGGATA CTTGTAACCA 351                                                    400
ferMCH2R    GTTTGCTTGT AGCGCCATCA TGACTGTGAT GAGTGTGGAC AGGTACTTGG
huMCH2R     GTTTGCTTGT AGCGCCATCA TGACTGTGAT GAGTGTGGAC AGGTACTTGG
dogMCH2R    GTTTGCCTGT AGTGCCATCA TGACTGTGAT GAGTATAGAC AGGTACTTGG
rhMCH2R     ATTTGCCTGT AGTGCCATCA TGACTGTAAT GAGTGTGGAC AGGTACTTTG 401                                                    450
ferMCH2R    CTCTCGTCCA ACCATTTCGA CTTACAAGTT GGAGAACGAG GTACAAGACC
huMCH2R     CTCTCGTCCA ACCATTTCGA CTTACAAGTT GGAGAACGAG GTACAAGACC
dogMCH2R    CTCTCGTCCA ACCATTTCGA CTTACAAGTT GGAGAACGAG GTACAAGACC
rhMCH2R     CCCTCGTCCA ACCATTTCGA CTGACAAGTT GGAGAACAAG GTACAAGACC 451                                                    500
ferMCH2R    ATCCGCATCA ATTTGGGCCT TTGGGCAGCT TCCTTCATTC TGGCGTTGCC
huMCH2R     ATCCGCATCA ATTTGGGCCT TTGGGCAGCT TCCTTCATTC TGGCGTTGCC
dogMCH2R    ATCCGCATCA ATTTGGGCCT TTGGGCAGCT TCCTTCATTC TGGCGCTGCC
rhMCH2R     ATCCGGATCA ATTTGGGCCT TTGGGCAGCT TCCTTTGTCC TGGCATTGCC
```

Fig. 2A

```
            501                                                 550
ferMCH2R    TGTCTGGGTC  TACTCGAAGG  TCATCAAATT  TAAAGACGGC  GTGGAGAGTT
huMCH2R     TGTCTGGGTC  TACTCGAAGG  TCATCAAATT  TAAAGACGGC  GTGGAGAGTT
dogMCH2R    TGTCTGGGTC  TACTCGAAGG  TCATCAAATT  TAAAGACGGC  GTGGAGAGTT
rhMCH2R     TGTCTGGATC  TACTCGAAGG  TCATCAAATT  TAAAGACGGT  GTCGAGAGTT 551                                                 600
ferMCH2R    GTGCTTTTGA  TTTAACATCC  CCTGACGATG  TACTCCGGTA  TACACTTTAT
huMCH2R     GTGCTTTTGA  TTTAACATCC  CCTGACGATG  TACTCCGGTA  TACACTTTAT
dogMCH2R    GTGCTTTTGA  TTTAACATCC  CCTGACGATG  TACTCCGGTA  TACACTTTAT
rhMCH2R     GTGCTTTTGA  TTTGACATCC  CCTGACGATG  TACTCTGGTA  TACACTTTAT 601                                                 650
ferMCH2R    CTGACGATAA  CAACTTTTTT  TTTTCCTTTG  CCTTTGATTT  TGGTGTGCTA
huMCH2R     CTGACGATAA  CAACTTTTTT  TTTTCCTTTG  CCTTTGATTT  TGGTGTGCTA
dogMCH2R    TTGACGATAA  CAACTTTTTT  TTTCCCTTTG  CCTTTGATTT  TGGTGTGCTA
rhMCH2R     TTGACAATAA  CAACTTTCTT  TTTCCCTCTA  CCCTTGATTT  TGGTGTGCTA 651                                                 700
ferMCH2R    TATTTTAATT  TTATGCTATA  CTTGGGAGAT  GTATCAACAG  AATAAGGATG
huMCH2R     TATTTTAATT  TTATGCTATA  CTTGGGAGAT  GTATCAACAG  AATAAGGATG
dogMCH2R    TATTTTAATT  TTATGCTATA  CTTGGGAGAT  GTATCAACAG  AATAAAGATG
rhMCH2R     TATTTTAATT  TTATGCTATA  CTTGGGAGAT  GTATCAACAG  AATAAGGATG 701                                                 750
ferMCH2R    CCAGATGTTA  CAACCCCAGT  GTTCCAAAAG  AGAGAGTGAT  GAAGCTGACA
huMCH2R     CCAGATGTTA  CAACCCCAGT  GTTCCAAAAG  AGAGAGTGAT  GAAGCTGACA
dogMCH2R    CAAGATGTTA  CAATCCCAGT  GTTCCAAAAG  AGAGAGTGAT  GAAGCTGACA
rhMCH2R     CCAGATGTTG  CAATCCCAGC  GTACCAAAAC  AGAGAGTGAT  GAAGTTGACA 751                                                 800
ferMCH2R    AAGATGGTGC  TGGTGTTGGT  GGCAGTCTTT  ATCCTGAGTG  CTGCCCCCTA
huMCH2R     AAGATGGTGC  TGGTGTTGGT  GGCAGTCTTT  ATCCTGAGTG  CTGCCCCCTA
dogMCH2R    AAGATGGTGC  TGGTGCTGGT  GGCGGTCTTT  ATCCTAAGTG  CTGCCCCCTA
rhMCH2R     AAGATGGTGC  TGGTGCTGGT  GGCAGTCTTT  ATCCTAAGTG  CTGCCCCTTA 801                                                 850
ferMCH2R    CCATGTGATA  CAACTGGTGA  ATTTACAGAT  GGAGCAGCCC  ACACTGGCCT
huMCH2R     CCATGTGATA  CAACTGGTGA  ATTTACAGAT  GGAGCAGCCC  ACACTGGCCT
dogMCH2R    CCACGTGATA  CAACTGGTGA  ACTTAAAGAT  GCAGCAGCCC  ACACTGGCCT
rhMCH2R     TCATGTGATA  CAACTGGTGA  ACTTACAGAT  GGAACAGCCC  ACACTGGCCT 851                                                 900
ferMCH2R    TCCATGTAGG  CTATTATCTC  TCCATCTGTT  TCAGCTATGC  CAGCAGCAGC
huMCH2R     TCCATGTAGG  CTATTATCTC  TCCATCTGTT  TCAGCTATGC  CAGCAGCAGC
dogMCH2R    TCCATGTAGG  CTATTATCTC  TCCATCTGTT  TCAGCTATGC  CAGCAGCAGC
rhMCH2R     TCTATGTGGG  TTATTACCTC  TCCATCTGTC  TCAGCTATGC  CAGCAGCAGC 901                                                 950
ferMCH2R    ATTAATCCTT  TCCTCTACAT  CATGCTGAGT  GGAAATTTCC  GGAAACGCCT
huMCH2R     ATTAATCCTT  TCCTCTACAT  CATGCTGAGT  GGAAATTTCC  GGAAACGCCT
dogMCH2R    ATTAACCCTT  TCCTCTACAT  CATGCTGAGT  GGAAATTTCC  GGAAACGCCT
rhMCH2R     ATTAACCCTT  TTCTCTACAT  CCTGCTGAGT  GGAAATTTCC  AGAAACGTCT 951                                                1000
ferMCH2R    GCCTCAAGTG  CAAAGAAGAG  TGACTGAGAG  GGAAATCAAC  AATATGGGAA
huMCH2R     GCCTCAAGTG  CAAAGAAGAG  TGACTGAGAG  GGAAATCAAC  AATATGGGAA
dogMCH2R    ACCTCAAGTA  CAAAGGAGAG  TGACTGAGA.  ....AATCAAC  AATATAG...
rhMCH2R     GCCTCAAATC  CAAAGGAGAG  TGACTGACAA  GGAAATCAAA  AATATGGGAA
```

Fig. 2B

```
              1001                 1023
ferMCH2R   ACACTCTGAA ATCACACTTT TAG  (SEQ ID NO: 6)
huMCH2R    ACACTCTGAA ATCACACTTT TAG  (SEQ ID NO: 8)
dogMCH2R   .......... .......... ...  (SEQ ID NO: 5)
rhMCH2R    ACACTCTGAA ATCACACTTT TAG  (SEQ ID NO: 7)
```

Fig. 2C

RHESUS MONKEY, DOG AND FERRET MELANIN-CONCENTRATING HORMONE TYPE 2 RECEPTOR

CROSS-REFERENCE TO RELATED APPLICATIONS

The present application claims priority to provisional application U.S. Ser. No. 60/294,747, filed May 31, 2001, hereby incorporated by reference herein.

BACKGROUND OF THE INVENTION

The references cited in the present application are not admitted to be prior art to the claimed invention.

Neuropeptides present in the hypothalamus play a major role in mediating the control of body weight. (Flier, et al., 1998. *Cell*, 92, 437–440.) Melanin-concentrating hormone (MCH) is a cyclic 19-amino acid neuropeptide synthesized as part of a larger pre-prohormone precursor in the hypothalamus which also encodes neuropeptides NEI and NGE. (Nahon, et al., 1990. *Mol. Endocrinol.* 4, 632–637.) MCH was first identified in salmon pituitary, and in fish MCH affects melanin aggregation thus affecting skin pigmentation. In trout and in eels MCH has also been shown to be involved in stress induced or CRF-stimulated ACTH release. (Kawauchi, et al., 1983. *Nature* 305, 321–323.)

In humans two genes encoding MCH have been identified that are expressed in the brain. (Breton, et al., 1993. *Mol. Brain Res.* 18, 297–310.) In mammals MCH has been localized primarily to neuronal cell bodies of the hypothalamus which are implicated in the control of food intake, including perikarya of the lateral hypothalamus and zona inertia. (Knigge, et al., 1996. *Peptides* 17, 1063–1073.)

Pharmacological and genetic evidence suggest that the primary mode of MCH action is to promote feeding (orexigenic). MCH mRNA is up regulated in fasted mice and rats and in the ob/ob mouse. (Qu, et al., 1996. *Nature* 380, 243–247.) Injection of MCH centrally (ICV) stimulates food intake and MCH antagonizes the hypophagic effects seen with α melanocyte stimulating hormone (αMSH). (Qu, et al., 1996. *Nature* 380, 243–247.) MCH deficient mice are lean, hypophagic and have increased metabolic rate. (Shimada, et al., 1998. *Nature* 396, 670–673.) Transgenic mice overexpressing MCH are hyperphagic and develop insulin resistance and mild obesity. (Ludwig, et al., 2001. *J. Clin. Invest.* 107, 379–386.)

MCH action is not limited to modulation of food intake as effects on the hypothalamic-pituitary-axis have been reported. (Nahon, 1994. *Critical Rev. in Neurobiol.* 8, 221–262.) MCH can modulate stress-induced release of ACTH. (Nahon, 1994. *Critical Rev. in Neurobiol.* 8, 221–262.)

Several references describe a receptor that is indicated to bind MCH ("MCH-1R"). (Chambers, et al., 1999. *Nature* 400, 261–265, Saito, et al., 1999. *Nature* 400, 265–269, Bächner, et al., 1999. *FEBS Letters* 457:522–524, Shimomura, et al., 1999. *Biochemical and Biophysical Research Communications* 261, 622–626.)

SUMMARY OF THE INVENTION

The present invention identifies the presence of MCH-2R in the dog, ferret and rhesus monkey. MCH-2R is a G-protein coupled receptor that responds to MCH and is distinct from MCH-1R. MCH-2R polypeptide and nucleic acid sequences related to the dog, ferret, and rhesus monkey MCH-2R are described herein along with uses of such polypeptides and nucleic acids.

Comparing the full-length MCH-2R amino acid and nucleic acid sequences of the dog, ferret, rhesus monkey, and human points to sequences that are unique for these different species and sequences shared by two or more species. The full length amino acid sequence for the dog, ferret, rhesus monkey and human are provided by SEQ. ID. NOs. 1–4. The full length cDNA sequence encoding dog, ferret rhesus monkey and human are provided by SEQ. ID. NOs. 5–8.

Thus, a first aspect of the present invention describes a purified polypeptide comprising an amino acid sequence region of at least ten amino acids that is common to the dog, ferret, and rhesus monkey MCH-2R, but is not present in the human MCH-2R. Examples of such polypeptides comprise an amino acid sequence selected from group consisting of SEQ. ID. NO. 9, SEQ. ID. NO. 10, and SEQ. ID. NO. 11.

Reference to the presence of a common region or sequence does not exclude the presence of additional regions which may or may not be present in the dog, ferret, or rhesus monkey MCH-2R. For example, a polypeptide comprising SEQ. ID. NOs. 9, 10 or 11, may have additional amino acid regions having human, dog, ferret, rhesus monkey MCH-2R sequences, or sequences not in the human, dog, ferret, or rhesus monkey MCH-2R.

A "purified polypeptide" represents at least 10% of the total protein present in a sample or preparation. In preferred embodiments, the purified polypeptide represents at least about 50%, at least about 75%, or at least about 95% of the total protein in a sample or preparation. Reference to "purified polypeptide" does not require that the polypeptide has undergone any purification and may include, for example, chemically synthesized polypeptide that has not been purified.

Another aspect of the present invention describes a purified nucleic acid comprising a nucleotide sequence region encoding a polypeptide having an amino acid sequence region that is common to the dog, ferret, and rhesus monkey MCH-2R, but is not present in the human MCH-2R. Examples of such nucleic acid comprise a nucleic acid sequence encoding a polypeptide selected from group consisting of SEQ. ID. NO. 9, SEQ. ID. NO. 10, and SEQ. ID. NO. 11.

A "purified nucleic acid" represents at least 10% of the total nucleic acid present in a sample or preparation. In preferred embodiments, the purified nucleic acid represents at least about 50%, at least about 75%, or at least about 95% of the total nucleic acid in a sample or preparation. Reference to "purified nucleic acid" does not require that the nucleic acid has undergone any purification and may include, for example, chemically synthesized nucleic acid that has not been purified.

Another aspect of the present invention describes a purified nucleic acid having a nucleotide sequence region at least eleven nucleotides in length that is common to the dog, ferret, and rhesus monkey MCH-2R, but is not present in the human MCH-2R. Examples of such sequences are provided by SEQ. ID. NO. 12, SEQ. ID. NO. 13, SEQ. ID. NO. 14, SEQ. ID. NO. 15 and the complements thereof.

Another aspect of the present invention describes a recombinant nucleic acid comprising a nucleotide sequence that either (a) encodes a polypeptide having an amino acid sequence region that is common to the dog, ferret, and rhesus monkey MCH-2R, but is not present in the human MCH-2R; or (b) provides a sequence region that is common to the dog, ferret, and rhesus monkey MCH-2R, but is not present in the human MCH-2R.

A "recombinant nucleic acid" is a nucleic acid containing one or more regions not naturally associated with each other. Recombinant nucleic acid can be present in a genome or outside of the genome.

Another aspect of the present invention describes a recombinant cell comprising an expression vector that comprises a nucleotide sequence encoding an amino acid sequence region that is common to the dog, ferret, and rhesus monkey MCH-2R, but is not present in the human MCH-2R. The sequence is coupled to a promoter recognized by the cell.

Another aspect of the present invention describes a recombinant cell made by a process involving use of an expression vector comprising a nucleotide sequence encoding an amino acid sequence region that is common to the dog, ferret, and rhesus monkey MCH-2R, but is not present in the human MCH-2R.

Another aspect of the present invention describes a method of measuring the ability of a compound to affect MCH-2R activity. The method comprises the steps of: (a) contacting a recombinant cell with the compound, wherein the cell comprises a recombinant nucleic acid expressing a functional MCH-2R; and (b) measuring MCH-2R activity. The functional MCH-2R expressed by the cell has an amino acid sequence region that is common to the dog, ferret, and rhesus monkey MCH-2R, but is not present in the human MCH-2R.

Another aspect of the present invention describes a method of preparing a MCH-2R polypeptide. The method comprises the step of growing a recombinant cell under conditions where the polypeptide is expressed from recombinant nucleic acid. The recombinant nucleic acid encodes a functional MCH-2R containing an amino acid sequence region that is common to the dog, ferret, and rhesus monkey MCH-2R, but is not present in the human MCH-2R.

Another aspect of the present invention describes a method of evaluating the ability of an MCH-2R active compound to exert an in vivo effect. The method comprises the steps of identifying an MCH-2R active compound, and measuring the effect of the compound on a rhesus monkey, a dog, or a ferret.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

BRIEF DESCRIPTION OF THE DRAWINGS

FIG. 1 provides an amino acid sequence comparison of the dog (SEQ. ID. NO. 1), ferret (SEQ. ID. NO. 2), rhesus monkey (SEQ. ID. NO. 3) and human MCH-2R (SEQ. ID. NO. 4).

FIGS. 2A, 2B and 2C provide a comparison of cDNA sequences for the dog (SEQ. ID. NO. 5), ferret (SEQ. ID. NO. 6), rhesus monkey (SEQ. ID. NO. 7) and human MCH-2R (SEQ. ID. NO. 8).

DETAILED DESCRIPTION OF THE INVENTION

Figure 3:
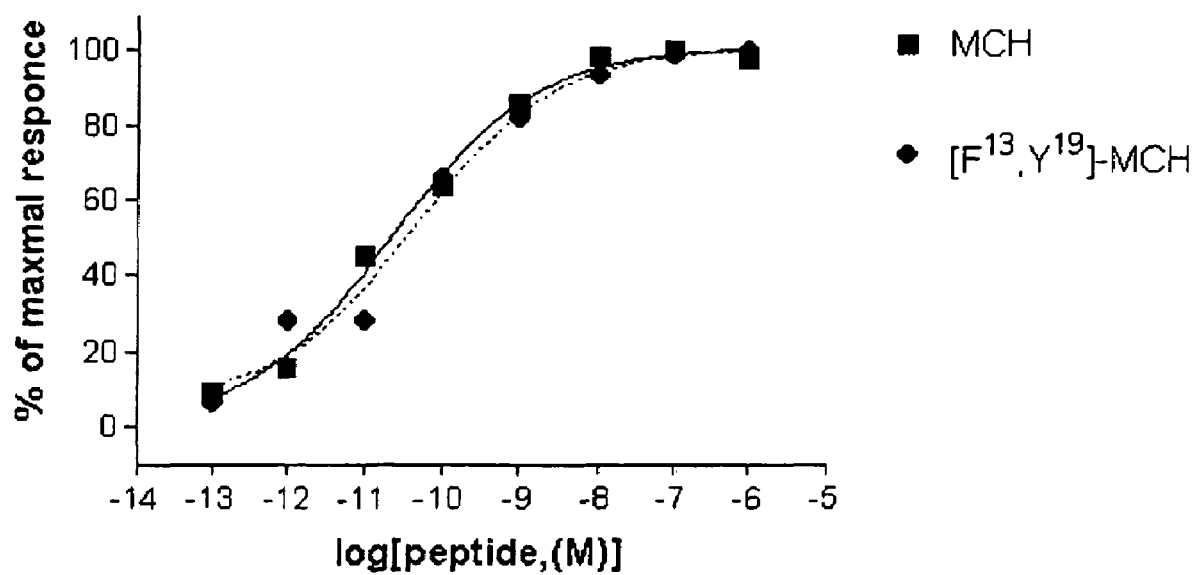
FIG. 3 illustrates the ability of MCH and [Phe$^{13}$, Tyr$^{19}$]-MCH to cause a dose-dependent increase in intracellular calcium levels in HEK293T cells transiently expressing rhesus MCH-2R.

The identification of the MCH-2R in the dog, ferret, and rhesus monkey provides MCH-2R amino acid and nucleic acid sequence information and a model for evaluating the effect of compounds that modulate MCH-2R activity. Dog, ferret and rhesus monkey MCH-2R sequence information have a variety of uses including being used to produce MCH-2R polypeptides and nucleic acids.

A preferred use of MCH-2R amino acid and nucleic acid sequences is to produce MCH-2R functional polypeptides that can be used in the initial identification of compounds binding to MCH-2R and modulating MCH-2R activity. The in vivo activity of such compounds can then be evaluated using, for example, a dog, ferret or rhesus monkey.

Compounds modulating MCH-2R activity have a variety of different uses including utility as a tool to further study MCH-2R activity and as an agent to achieve a beneficial effect in a patient. Modulating MCH-2R activity includes evoking a response at the receptor and altering a response evoked by a MCH-2R agonist or antagonist.

Beneficial effects of modulating MCH-2R activity include achieving one or more of the following in a patient: weight loss, weight gain, cancer treatment (e.g., colon or breast), pain reduction, diabetes treatment, stress reduction and sexual dysfunction treatment. A patient is a mammal, preferably a human. Reference to patient does not necessarily indicate the presence of a disease or disorder. The term patient includes subjects treated prophylactically and subjects afflicted with a disease or disorder.

Preferably, MCH-2R activity is modulated to treat diabetes, to obtain a weight loss, or to obtain a weight gain. Diabetes mellitus can be treated by, for example, one or both of the following: enhancing glucose tolerance and decreasing insulin resistance.

Excessive weight is a contributing factor to different diseases including hypertension, diabetes, dyslipidemias, cardiovascular disease, gall stones, osteoarthritis and certain forms of cancers. Bringing about a weight loss can be used, for example, to reduce the likelihood of such diseases and as part of a treatment for such diseases. Weight reduction can be achieved by, for example, one or more of the following: reducing appetite, increasing metabolic rate, reducing fat intake and reducing carbohydrate craving.

Increasing weight is particularly useful for a patient having a disease or disorder, or under going a treatment, accompanied by weight loss. Examples of diseases or disorders accompanied by weight loss include anorexia, AIDS, wasting, cachexia, and frail elderly. Examples of treatments accompanied by weight loss include chemotherapy and radiation therapy.

MCH-2R Polypeptides

MCH-2R polypeptides featured herein contain a region of SEQ. ID. NOs. 1, 2, or 3 that is at least 9 contiguous amino acids in length. The MCH-2R polypeptide can be made up of only MCH-2R sequences from SEQ. ID. NOs. 1–3 or can be a chimeric polypeptide. MCH-2R polypeptides have a variety of uses, such as providing a component for a functional receptor; being used as an immunogen to produce antibodies binding to MCH-2R; being used as a target to identify compounds binding to the MCH-2R; and being used in assays to measure the ability of a compound to affect MCH-2R activity.

Chimeric polypeptides contain one or more regions from MCH-2R and one or more regions not from MCH-2R. The region(s) not from MCH-2R can be used, for example, to achieve a particular purpose or to produce a polypeptide that can substitute for MCH-2R or a fragment thereof. Particular purposes that can be achieved using MCH-2R polypeptides that are chimeric include providing a marker for isolation, functional analysis of different receptor regions, enhancing an immune response, and altering G-protein coupling.

MCH-2R polypeptides may contain a sequence region that is unique to either the dog, ferret, or rhesus monkey, or is present in two or more of these different animals. FIG. 1 illustrates an amino acid sequence comparison of the dog, ferret, rhesus monkey, and human MCH-2R. The sequence comparison provided in FIG. 1 identifies unique and common amino acid sequences.

A "unique" amino acid sequence differs from at least the human sequence, and preferably also from either the dog and ferret, dog and rhesus monkey, ferret and rhesus monkey, or dog and rhesus monkey. In an embodiment of the present invention, the MCH-2R polypeptide comprises or consists of an amino acid sequence at least 9 bases in length that is unique for at least one of SEQ. ID. NOs. 1–3. In additional embodiments, the unique sequence is at least 18 amino acids in length, at least 27 amino acids in length, or at least 54 amino acids in length.

A "common" amino acid sequence is with respect to at least two of the dog, ferret, and rhesus monkey sequences. In an embodiment of the present invention, the MCH-2R polypeptide has an amino acid sequence region at least 9 amino acids in length that is common to the dog, ferret, and rhesus monkey MCH-2R, but is not present in the human MCH-2R. Examples of such polypeptides comprise an amino acid sequence selected from group consisting of:
SEQ. ID. NO. 9 DLVHIIGMPF;
SEQ. ID. NO. 10 LTSWRTRYKT; and
SEQ. ID. NO. 11 KMVLVLVAVF.

Additional MCH-2R polypeptides described herein include functional G-protein receptors that respond to MCH and (1) have a sequence similarity of at least about 98% with either SEQ. ID. NOs. 1, 2 or 3; or (2) provide a sequence with up to about 10 alterations from SEQ. ID. NOs. 1, 2, or 3. Sequence similarity for polypeptides can be determined by BLAST. (Altschul, et al., 1997. *Nucleic Acids Res.* 25, 3389–3402, hereby incorporated by reference herein.) In one embodiment sequence similarity is determined using tBLASTn search program with the following parameters: MATRIX:BLOSUM62, PER RESIDUE GAP COST: 11, and Lambda ratio: 1.

Alterations to amino acid sequences are additions, deletions, and substitutions. In different embodiments the MCH-2R polypeptide has 1, 2, 3, 4, 5, 6, 7, 8, 9, or 10 alterations from SEQ. ID. NOs. 1, 2, or 3.

Polypeptides can be produced using standard techniques including those involving chemical synthesis and those involving biochemical synthesis. Techniques for chemical synthesis of polypeptides are well known in the art. (See e.g., Vincent, in *Peptide and Protein Drug Delivery*, New York, N.Y., Dekker, 1990.)

Biochemical synthesis techniques for polypeptides are also well known in the art. Such techniques employ a nucleic acid template for polypeptide synthesis. The genetic code providing the sequences of nucleic acid triplets coding for particular amino acids is well known in the art. (See, e.g., Lewin *GENES IV*, p. 119, Oxford University Press, 1990.) Examples of techniques for introducing nucleic acid into a cell and expressing the nucleic acid to produce protein are provided in references such as Ausubel, *Current Protocols in Molecular Biology*, John Wiley, 1987–1998, and Sambrook, et al., in *Molecular Cloning, A Laboratory Manual, 2nd* Edition, Cold Spring Harbor Laboratory Press, 1989.

Functional MCH-2R

Functional MCH-2R transduces a G-protein coupled intracellular signal upon ligand binding. The identification of the amino acid and nucleic acid MCH-2R sequences provide tools for producing dog, ferret, and rhesus monkey MCH-2R, for obtaining MCH-2R from other sources, for producing MCH-2R chimeric G-protein coupled receptors, and for producing functional derivatives of the dog, ferret and rhesus monkey MCH-2R.

MCH-2R polypeptides from different sources can be identified and obtained based on their sequence similarity to the dog, ferret, or rhesus monkey MCH-2R. The amino acid and nucleic acid sequences of the dog, ferret, and rhesus monkey MCH-2R can be used to help identify and obtain additional MCH-2R polypeptides. For example, SEQ. ID. NOs. 1, 2 or 3 can be used to design degenerative nucleic acid probes or primers for identifying and cloning nucleic acid encoding for a MCH-2R polypeptide, and SEQ. ID. NOs. 5, 6, or 7, the complement of SEQ. ID. NOs. 5, 6, or 7, and fragments thereof, can be used under conditions of moderate stringency to identify and clone nucleic acid encoding MCH-2R polypeptides.

The use of degenerative probes and moderate stringency conditions for cloning is well known in the art. Examples of such techniques are described by Ausubel, *Current Protocols in Molecular Biology*, John Wiley, 1987–1998, and Sambrook, et al., in *Molecular Cloning, A Laboratory Manual, 2nd* Edition, Cold Spring Harbor Laboratory Press, 1989.

Starting with MCH-2R obtained from a particular source, derivatives can be produced having receptor activity. Such derivatives include polypeptides with amino acid substitutions, additions and deletions. Changes to MCH-2R to produce a derivative having essentially the same properties should be made outside of the MCH-2R binding domain and in a manner not altering the tertiary structure. The ability of a polypeptide to have MCH-2R activity can be confirmed using techniques such as those measuring G-protein activity.

Differences in naturally occurring amino acids are due to different R groups. An R group affects different properties of the amino acid such as physical size, charge, and hydrophobicity. Amino acids can be divided into different groups as follows: neutral and hydrophobic (alanine, valine, leucine, isoleucine, proline, tyrptophan, phenylalanine, and methionine); neutral and polar (glycine, serine, threonine, tryosine, cysteine, asparagine, and glutamine); basic (lysine, arginine, and histidine); and acidic (aspartic acid and glutamic acid).

Generally, in substituting different amino acids it is preferable to exchange amino acids having similar properties. Substituting different amino acids within a particular group, such as substituting valine for leucine, arginine for lysine, and asparagine for glutamine are good candidates for not causing a change in polypeptide functioning.

Changes outside of different amino acid groups can also be made. Preferably, such changes are made taking into account the position of the amino acid to be substituted in the polypeptide. For example, arginine can substitute more freely for nonpolar amino acids in the interior of a polypeptide then glutamate because of its long aliphatic side chain. (See, Ausubel, *Current Protocols in Molecular Biology*, John Wiley, 1987–1998, Supplement 33 Appendix 1C.)

MCH-2R Antibodies

Antibodies recognizing MCH-2R can be produced using a polypeptide containing SEQ. ID. NOs. 1, 2, or 3, or a fragment thereof as an immunogen. In an embodiment of the present invention, a polypeptide used as an immunogen consists of a polypeptide of SEQ. ID. NOs. 1, 2, or 3 or a fragment at least 9 amino acids in length.

Antibodies to MCH-2R have different uses such as being used to identify the presence of MCH-2R and to isolate MCH-2R polypeptides. Identifying the presence of MCH-2R can be used, for example, to identify cells producing MCH-2R. Such identification provides an additional source of MCH-2R and can be used to distinguish cells known to produce MCH-2R from cells that do not produce MCH-2R.

Techniques for producing and using antibodies are well known in the art. Examples of such techniques are described in Ausubel, *Current Protocols in Molecular Biology*, John Wiley, 1987–1998, Harlow, et al., *Antibodies, A Laboratory Manual*, Cold Spring Harbor Laboratory, 1988, and Kohler, et al., *Nature* 256:495–497, 1975.

Binding Assay

MCH-2R or a fragment thereof can be used in binding studies to identify compounds binding to the receptor. Such studies can be performed using different formats including competitive and non-competitive formats.

The particular MCH-2R sequence involved in ligand binding can be identified using labeled compounds that bind to the receptor and different receptor fragments. Different strategies can be employed to select fragments to be tested to narrow down the binding region. Examples of such strategies include testing consecutive fragments about 15 amino acids in length starting at the N-terminus, and testing longer length fragments. If longer length fragments are tested, a fragment binding to a compound can be subdivided or mutated to further locate the binding region. Fragments used for binding studies can be generated by recombinant nucleic acid techniques.

Preferably, binding studies are performed using MCH-2R expressed from a recombinant nucleic acid. In an embodiment of the present invention, a recombinantly expressed MCH-2R consists of the amino acid sequence of SEQ. ID. NO. 1, SEQ. ID. NO. 2, or SEQ. ID. NO. 3.

Binding assays can be performed using individual compounds or preparations containing different numbers of compounds. A preparation containing different numbers of compounds having the ability to bind to MCH-2R can be divided into smaller groups of compounds that can be tested to identify the compound(s) binding to MCH-2R.

Binding assays can be performed using MCH-2R present in different environments. Such environments include, for example, cell extracts and purified cell extracts containing MCH-2R; and also include, for example, the use of a purified MCH-2R receptor polypeptide which is introduced into a different environment.

The identification of MCH as an agonist for MCH-2R provides a means for producing receptor activity, and provides a target for binding to the receptor and for stimulating receptor activity. MCH agonists can be designed based on the structure of MCH. Examples of MCH agonists include human MCH, salmon MCH, and derivatives thereof. Suitable derivatives can be identified empirically, for example, by deleting or substituting one or more amino acids of human MCH and testing the resulting polypeptide. Techniques for producing a polypeptide of a particular sequence are well known in the art. (Phe$^{13}$Tyr$^{19}$)-MCH is an example of an MCH derivative that binds MCH-2R.

Different types of labels for MCH agonists can be employed. Examples of such labels include radiolabels, luminescent molecules, haptens and enzyme substrates. The ability of a particular label to interfere with binding can be determined by comparing the ability of MCH containing the particular label to compete against unlabeled MCH.

Functional Assays

Assays involving a functional G-protein receptor containing one or more MCH-2R regions can be employed for different purposes such as selecting for compounds active at MCH-2R, evaluating the ability of a compound to affect receptor activity, and mapping the activity of different MCH-2R regions. MCH-2R activity can be measured using different techniques such as detecting a change in the intracellular conformation of MCH-2R, measuring G-protein activity, or measuring the level of intracellular messengers.

Recombinantly expressed receptor can be used to facilitate determining whether a compound is active at that receptor or another receptor. For example, MCH-2R can be expressed by an expression vector in a cell line such as HEK 293, COS 7, or CHO, not normally expressing the receptor, wherein the same cell line without the expression vector or with an expression vector not encoding MCH-2R can act as a control.

Techniques for measuring different G-protein activities, such as Gi, Gs, and Gq are well known in the art. Gi and Gs activity can be measured using techniques such as a melonaphore assay, assays measuring cAMP production, assays measuring inhibition of cAMP accumulation, and assays measuring binding of 35S-GTP. cAMP can be measured using different techniques such as a radioimmunoassay and indirectly by cAMP responsive gene reporter proteins.

Gq activity can be measured using techniques such as those measuring intracellular $Ca^{2+}$. Examples of techniques well known in the art that can be employed to measure $Ca^{2+}$ include the use of dyes such as Fura-2 and the use of $Ca^{2+}$-bioluminescent sensitive reporter proteins such as aequorin. An example of a cell line employing aequorin to measure G-protein activity is HEK293/aeq17. (Button, et al., 1993. *Cell Calcium* 14, 663–671, and Feighner, et al., 1999. *Science* 284, 2184–2188, both of which are hereby incorporated by reference herein.)

Chimeric MCH-2R can be used to assay for compounds active at the receptor and to obtain information concerning different regions of the receptor. A chimeric MCH-2R receptor contains an N-terminal extracellular domain; a transmembrane domain made up of transmembrane regions (preferably 7 transmembrane regions), extracellular loop regions, and intracellular loop regions; and an intracellular carboxy terminus domain; where one or more domains comprises a unique or common region of SEQ. ID. NOs. 1–3 of at least 9 contiguous amino acids. In different embodiments, a chimeric MCH-2R contains the extracellular domain of MCH-2R present in either SEQ. ID. NOs. 1, 2, or 3; the unique or common region contains at least 18 contiguous amino acids present in SEQ. ID. NOs. 1, 2 or 3; or a common region having the sequence of SEQ. ID. NOs. 9, 10 or 11 is present.

The specificity of G-protein coupling is determined by intracellular domain(s). Chimeric MCH-2R can be produced to functionally couple to a desired G-protein. Techniques for producing chimeric receptors and measuring G-protein coupled responses are provided in, for example, International Application Number WO 97/05252, U.S. Pat. No. 5,981,195, and U.S. Pat. No. 5,264,565.

Functional assays can be performed using individual compounds or preparations containing different compounds. A preparation containing different compounds where one or more compounds affect MCH-2R activity can be divided into smaller groups of compounds to identify the compound(s) affecting MCH-2R activity.

Functional assays can be performed using recombinantly produced MCH-2R present in different environments. Such environments include, for example, cells expressing recombinant nucleic acid encoding for a functional MCH-2R, cell extracts and purified cell extracts containing the MCH-2R expressed from recombinant nucleic acid and an appropriate membrane for the polypeptide; and the use of a purified MCH-2R produced by recombinant means that is introduced into a different environment suitable for measuring G-protein activity.

Screening for MCH-2R receptor active compounds is facilitated through the use of a MCH agonist in the assay. The use of a MCH agonist in a screening assay provides for MCH-2R activity. The effect of test compounds on such activity can be measured to identify, for example, allosteric modulators and antagonists.

MCH-2R Nucleic Acid

MCH-2R nucleic acid featured herein includes nucleic acid containing a region encoding a MCH-2R polypeptide having a unique or common region at least 9 amino acids in length that is present in SEQ. ID. NOs. 1, 2, or 3, and nucleic acid containing a unique or common region of at least 11 contiguous bases that is present in at least one of SEQ. ID. NOs. 5, 6, or 7 or the complement thereof. MCH-2R nucleic acid have a variety of uses, such as being used as a hybridization probe or PCR primer to identify the presence of MCH-2R nucleic acid; being used as a hybridization probe or PCR primer to identify nucleic acid encoding receptors related to MCH-2R and being used for recombinant expression of MCH-2R polypeptides.

MCH-2R nucleic acid may be associated with nucleic acid not from MCH-2R. Regions in MCH-2R nucleic acid that do not encode for a MCH-2R segment or are not found in SEQ. ID. NOs. 5, 6, 7, or the complement thereof, if present, are preferably chosen to achieve a particular purposes. Examples of additional regions that can be used to achieve a particular purpose include capture regions that can be used as part of a sandwich assay, reporter regions that can be probed to indicate the presence of the nucleic acid, expression vector regions, and regions encoding other polypeptides.

MCH-2R nucleic acid may contain a sequence region that is unique to either the dog, ferret, or rhesus monkey, or is present in two or more of these different animals. FIGS. 2A–2C illustrate a nucleotide sequence comparison of the dog, ferret, human, and rhesus monkey MCH-2R encoding nucleic acid. The sequence comparison provided in FIGS. 2A–2C identifies unique and common nucleotide sequences.

A "unique" nucleotide sequence differs from at least the human sequence, and preferably also from either the dog and ferret, dog and rhesus monkey, ferret and rhesus monkey, or dog and rhesus monkey. In embodiments of the present invention, the MCH-2R nucleic acid comprises or consists of a nucleotide sequence at least 18 bases in length that is unique for at least one of SEQ. ID. NOs 5, 6, or 7 or the complement thereof. In additional embodiments the unique sequence is at least 36 or 54 bases in length.

A "common" nucleotide sequence is with respect to at least two of the dog, ferret, and rhesus monkey sequences. In an embodiment of the present invention, the MCH-2R nucleic acid has a nucleotide sequence at least 11 bases in length that is common to the dog, ferret, and rhesus monkey MCH-2R, but is not present in the human MCH-2R. Examples of such nucleic acid comprise a nucleotide sequence selected from group consisting of:

SEQ. ID. NO. 12 CTATAATAAGGTCCAGAA;
SEQ. ID. NO. 13 CACATCATTGGAATGCC;
SEQ. ID. NO. 14 ACAAGTTGGAGAAC; and
SEQ. ID. NO. 15 AGAGTGACTGA.

Additional MCH-2R nucleic acid includes nucleic acid encoding a functional G-protein that responds to MCH where (1) the encoded G-protein has a sequence similarity of at least 98% with SEQ. ID. NOs. 1, 2, or 3, (2) the encoded G-protein has sequence differing from SEQ. ID. NOs. 1, 2, or 3 by up to 10 alterations; or (3) the nucleic acid has a sequence similarity of at least about 98% with SEQ. ID. NO. 5, 6, or 7. Sequence similarity for nucleic acid can be determined by FASTA. (Pearson 1990. *Methods in Enzymology* 183, 63–98, hereby incorporated by reference herein.) In one embodiment, sequence similarity is determined using the FASTA search program with the following parameters: MATRIX: BLOSUM50, GAP PENALTIES: open=–12; residue=–2.

The guidance provided in the present application can be used to obtain nucleic acid sequence encoding MCH-2R related receptors from different sources and to construct a receptor having MCH-2R activity. Obtaining nucleic acids encoding MCH-2R related receptors from different sources is facilitated using sets of degenerative probes and primers and by the proper selection of hybridization conditions. Sets of degenerative probes and primers are produced taking into account the degeneracy of the genetic code. Adjusting hybridization conditions is useful for controlling probe or primer specificity to allow for hybridization to nucleic acids having similar sequences.

Techniques employed for hybridization detection and PCR cloning are well known in the art. Nucleic acid detection techniques are described, for example, in Sambrook, et al., in *Molecular Cloning, A Laboratory Manual*, $2^{nd}$ Edition, Cold Spring Harbor Laboratory Press, 1989. PCR cloning techniques are described, for example, in White, *Methods in Molecular Cloning*, volume 67, Humana Press, 1997.

MCH-2R probes and primers can be used to screen nucleic acid libraries containing, for example, genomic DNA or cDNA. Such libraries are commercially available, and can be produced using techniques such as those described in Ausubel, *Current Protocols in Molecular Biology*, John Wiley, 1987–1998.

Starting with a particular amino acid sequence and the known degeneracy of the genetic code, a large number of different encoding nucleic acid sequences can be obtained. The degeneracy of the genetic code arises because almost all amino acids are encoded for by different combinations of nucleotide triplets or "codons". The translation of a particular codon into a particular amino acid is well known in the art (see, e.g., Lewin *GENES IV*, p. 119, Oxford University Press, 1990). Amino acids are encoded for by codons as follows:

A=Ala=Alanine: codons GCA, GCC, GCG, GCU
C=Cys=Cysteine: codons UGC, UGU
D=Asp=Aspartic acid: codons GAC, GAU E=Glu=Glutamic acid: codons GAA, GAG
F=Phe=Phenylalanine: codons UUC, UUU
G=Gly=Glycine: codons GGA, GGC, GGG, GGU
H=His=Histidine: codons CAC, CAU
I=Ile=Isoleucine: codons AUA, AUC, AUU
K=Lys=Lysine: codons AAA, AAG
L=Leu=Leucine: codons UUA, UUG, CUA, CUC, CUG, CUU
M=Met=Methionine: codon AUG
N=Asn=Asparagine: codons AAC, AAU
P=Pro=Proline: codons CCA, CCC, CCG, CCU
Q=Gln=Glutamine: codons CAA, CAG
R=Arg=Arginine: codons AGA, AGG, CGA, CGC, CGG, CGU
S=Ser=Serine: codons AGC, AGU, UCA, UCC, UCG, UCU
T=Thr=Threonine: codons ACA, ACC, ACG, ACU
V=Val=Valine: codons GUA, GUC, GUG, GUU
W=Trp=Tryptophan: codon UGG
Y=Tyr=Tyrosine: codons UAC, UAU Nucleic acid having a desired sequence can be synthesized using chemical and biochemical techniques. Examples of chemical techniques are described in Ausubel, *Current Protocols in Molecular Biology*, John Wiley, 1987–1998, and Sambrook et al., in *Molecular Cloning, A Laboratory Manual*, $2^{nd}$ Edition, Cold Spring Harbor Laboratory Press, 1989.

Biochemical synthesis techniques involve the use of a nucleic acid template and appropriate enzymes such as DNA and/or RNA polymerases. Examples of such techniques include in vitro amplification techniques such as PCR and transcription based amplification, and in vivo nucleic acid replication. Examples of suitable techniques are provided by Ausubel, *Current Protocols in Molecular Biology*, John Wiley, 1987–1998, Sambrook et al., in *Molecular Cloning, A Laboratory Manual*, $2^{nd}$ Edition, Cold Spring Harbor Laboratory Press, 1989, and Kacian, et al., U.S. Pat. No. 5,480,784.

MCH-2R Probes

Probes for MCH-2R contain a region that can specifically hybridize to MCH-2R target nucleic acid under appropriate hybridization conditions and can distinguish target nucleic acid from one or more non-target nucleic acids. Probes for MCH-2R can also contain nucleic acid that is not complementary to MCH-2R nucleic acid.

Preferably, non-complementary nucleic acid that is present has a particular purpose such as being a reporter sequence or being a capture sequence. However, additional nucleic acid need not have a particular purpose as long as the additional nucleic acid does not prevent the MCH-2R probe from distinguishing between target and non-target.

Hybridization occurs through complementary nucleotide bases. Hybridization conditions determine whether two molecules, or regions, have sufficiently strong interactions with each other to form a stable hybrid.

The degree of interaction between two molecules that hybridize together is reflected by the Tm of the produced hybrid. The higher the Tm the stronger the interactions and the more stable the hybrid. Tm is affected by different factors well known in the art such as the degree of complementarity, the type of complementary bases present (e.g., A-T hybridization versus G-C hybridization), the presence of modified nucleic acid, and solution components. (E.g., Sambrook, et al., in *Molecular Cloning, A Laboratory Manual*, $2^{nd}$ Edition, Cold Spring Harbor Laboratory Press, 1989.)

Stable hybrids are formed when the Tm of a hybrid is greater than the temperature employed under a particular set of hybridization assay conditions. The degree of specificity of a probe can be varied by adjusting the hybridization stringency conditions. Detecting probe hybridization is facilitated through the use of a detectable label. Examples of detectable labels include luminescent, enzymatic, and radioactive labels.

Examples of stringency conditions are provided in Sambrook, et al., in *Molecular Cloning, A Laboratory Manual*, $2^{nd}$ Edition, Cold Spring Harbor Laboratory Press, 1989. An example of high stringency conditions is as follows: Prehybridization of filters containing DNA is carried out for 2 hours to overnight at 65° C. in buffer composed of 6×SSC, 5× Denhardt's solution, and 100 µg/ml denatured salmon sperm DNA. Filters are hybridized for 12 to 48 hours at 65° C. in prehybridization mixture containing 100 µg/ml denatured salmon sperm DNA and 5–20×$10^6$ cpm of $^{32}$P-labeled probe. Washing of filters is done at 37° C. for 1 hour in a solution containing 2×SSC, 0.1% SDS. This is followed by a wash in 0.1×SSC, 0.1% SDS at 50° C. for 45 minutes before autoradiography. Other procedures using conditions of high stringency would include, for example, either a hybridization step carried out in 5×SSC, 5× Denhardt's solution, 50% formamide at 42° C. for 12 to 48 hours or a washing step carried out in 0.2×SSPE, 0.2% SDS at 65° C. for 30 to 60 minutes.

Probes are composed of nucleic acids or derivatives thereof such as modified nucleic acid and peptide nucleic acid. Modified nucleic acid includes nucleic acid with one or more altered sugar groups, altered internucleotide linkages, and/or altered nucleotide purine or pyrimidine bases. References describing modified nucleic acid include WO 98/02582, U.S. Pat. No. 5,859,221 and U.S. Pat. No. 5,852,188, each of which are hereby incorporated by reference herein.

Recombinant Expression

MCH-2R polypeptides can be expressed from recombinant nucleic acid in a suitable host or in a test tube using a translation system. Recombinantly expressed MCH-2R polypeptides are preferably used in assays to screen for compounds that bind to MCH-2R and modulate the activity of the receptor.

Preferably, expression is achieved in a host cell using an expression vector. An expression vector contains recombinant nucleic acid encoding for a polypeptide along with regulatory elements for proper transcription and processing. The regulatory elements that may be present include those naturally associated with the recombinant nucleic acid and exogenous regulatory elements not naturally associated with the recombinant nucleic acid. Exogenous regulatory elements such as an exogenous promoter can be useful for expressing recombinant nucleic acid in a particular host.

Generally, the regulatory elements that are present in an expression vector include a transcriptional promoter, a ribosome binding site, a terminator, and an optionally present operator. Another preferred element is a polyadenylation signal providing for processing in eukaryotic cells. Preferably, an expression vector also contains an origin of replication for autonomous replication in a host cell, a selectable marker, a limited number of useful restriction enzyme sites, and a potential for high copy number. Examples of expression vectors are cloning vectors, modified cloning vectors, specifically designed plasmids and viruses.

Expression vectors providing suitable levels of polypeptide expression in different hosts are well known in the art. Mammalian expression vectors well known in the art include pcDNA3 (Invitrogen), pMC1neo (Stratagene), pXT1 (Stratagene), pSG5 (Stratagene), EBO-pSV2-neo (ATCC 37593), pBPV-1(8-2) (ATCC 37110), pdBPV-MMT-neo(342-12) (ATCC 37224), pRSVgpt (ATCC 37199), pRSVneo (ATCC 37198), pSV2-dhfr (ATCC 37146), pUCTag (ATCC 37460), pCI-neo (Promega) and .lambda.ZD35 (ATCC 37565). Bacterial expression vectors well known in the art include pET11a (Novagen), lambda gt11 (Invitrogen), pcDNAII (Invitrogen), and pKK223-3 (Pharmacia). Fungal cell expression vectors well known in the art include pYES2 (Invitrogen), Pichia expression vector (Invitrogen). Insect cell expression vectors well known in the art include Blue Bac III (Invitrogen).

Recombinant host cells may be prokaryotic or eukaryotic. Examples of recombinant host cells include the following: bacteria such as *E. coli*; fungal cells such as yeast; mammalian cells such as human, bovine, porcine, monkey and rodent; and insect cells such as Drosophila and silkworm derived cell lines. Commercially available mammalian cell lines include L cells L-M(TK.sup.-) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26) and MRC-5 (ATCC CCL 171).

To enhance expression in a particular host it may be useful to modify the sequence provided in SEQ. ID. NOs. 5, 6, or 7 to take into account codon usage of the host. Codon usage of different organisms are well known in the art. (See, Ausubel, *Current Protocols in Molecular Biology*, John Wiley, 1987–1998, Supplement 33 Appendix 1C.)

Expression vectors may be introduced into host cells using standard techniques. Examples of such techniques include transformation, transfection, lipofection, protoplast fusion, and electroporation.

Nucleic acid encoding an MCH-2R polypeptide can be expressed in a cell without the use of an expression vector by, for example, creating or introducing a recombinant nucleic acid encoding a MCH-2R polypeptide into the cell genome. Additionally, mRNA can be translated in various cell-free systems such as wheat germ extracts and reticulocyte extracts, as well as in cell based systems, such as frog oocytes. Introduction of mRNA into cell based systems can be achieved, for example, by microinjection.

Modulating MCH-2R Activity

Using the present application as a guide compounds able to modulate MCH-2R can be obtained and used to achieve a beneficial effect in a patient. Such effects can be obtained, for example, by altering weight or relieving stress using a compound active at MCH-2R.

Altering weight is particularly useful for gaining weight in an under weight patient or losing weight in an over weight patient. In addition, for example, farm animals can be treated to gain weight. Under weight patients include those having a body weight about 10% or less, 20% or less, or 30% or less, than the lower end of a "normal" weight range or Body Mass Index ("BMI"). Over weight patients include those having a body weight about 10% or more, 20% or more, 30% or more, or 50% or more, than the upper end of a "normal" weight range or BMI. "Normal" weight ranges are well known in the art and take into account factors such as a patient age, height, and body type.

BMI measures your height/weight ratio. It is determined by calculating weight in kilograms divided by the square of height in meters. The BMI "normal" range is 19–22.

MCH-2R modulating compounds can be provided in a kit. Such a kit typically contains an active compound in dosage forms for administration. A dosage form contains a sufficient amount of active compound such that a beneficial effect can be obtained when administered to a patient during regular intervals, such as 1 to 6 times a day, during the course of 1 or more days. Preferably, a kit contains instructions indicating the use of the dosage form for weight reduction (e.g., to treat obesity or overweight) or stress reduction, and the amount of dosage form to be taken over a specified time period.

Dosing for Therapeutic Applications

Guidelines for pharmaceutical administration in general are provided in, for example, *Remington's Pharmaceutical Sciences* 18$^{th}$ Edition, Ed. Gennaro, Mack Publishing, 1990, and *Modern Pharmaceutics* 2$^{nd}$ Edition, Eds. Banker and Rhodes, Marcel Dekker, Inc., 1990, both of which are hereby incorporated by reference herein.

MCH-2R active compounds having appropriate functional groups can be prepared as acidic or base salts. Pharmaceutically acceptable salts (in the form of water- or oil-soluble or dispersible products) include conventional non-toxic salts or the quaternary ammonium salts that are formed, e.g., from inorganic or organic acids or bases. Examples of such salts include acid addition salts such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate; and base salts such as ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine.

MCH-2R active compounds can be administered using different routes including oral, nasal, by injection, and transmucosally. Active ingredients to be administered orally as a suspension can be prepared according to techniques well known in the art of pharmaceutical formulation and may contain microcrystalline cellulose for imparting bulk, alginic acid or sodium alginate as a suspending agent, methylcellulose as a viscosity enhancer, and sweeteners/flavoring agents. As immediate release tablets, these compositions may contain microcrystalline cellulose, dicalcium phosphate, starch, magnesium stearate and lactose and/or other excipients, binders, extenders, disintegrants, diluents and lubricants.

When administered by nasal aerosol or inhalation, compositions can be prepared according to techniques well known in the art of pharmaceutical formulation. Such techniques can involve preparing solutions in saline, employing benzyl alcohol or other suitable preservatives, absorption promoters to enhance bioavailability, fluorocarbons, or other solubilizing or dispersing agents.

Routes of administration include intravenous (both bolus and infusion), intraperitoneal, subcutaneous, topical with or without occlusion, and intramuscular. Injectable solutions or suspensions known in the art include suitable non-toxic, parenterally-acceptable diluents or solvents, such as mannitol, 1,3-butanediol, water, Ringer's solution and isotonic sodium chloride solution. Dispersing or wetting and suspending agents, include sterile, bland, fixed oils, such as synthetic mono- or diglycerides; and fatty acids, such as oleic acid.

Rectal administration in the form of suppositories, include the use of a suitable non-irritating excipient, such as cocoa butter, synthetic glyceride esters or polyethylene glycols. These excipients are solid at ordinary temperatures, but liquidify and/or dissolve in the rectal cavity to release the drug.

Suitable dosing regimens for the therapeutic applications of the present invention are selected taking into account factors well known in the art including age, weight, sex and medical condition of the patient; the severity of the condition to be treated; the route of administration; the renal and hepatic function of the patient; and the particular compound employed.

Optimal precision in achieving concentrations of drug within the range that yields efficacy without toxicity requires a regimen based on the kinetics of the drug's availability to target sites. This involves a consideration of the distribution, equilibrium, and elimination of a drug. The daily dose for a patient is expected to be between 0.01 and 1,000 mg per adult patient per day.

EXAMPLES

Examples are provided below to further illustrate different features of the present invention. The examples also illustrate useful methodology for practicing the invention. These examples do not limit the claimed invention.

Example 1

Cloning Rhesus Monkey MCH-2R

The full-length coding sequence of rhesus MCH-2R was cloned from a rhesus brain. Two mix-base primers MCH3-1 (SEQ. ID. No. 16) (GGI ATG CCI TTY HTI ATH CAY CA) and MCH3-2 (SEQ. ID. NO. 17) (ARY TGI ADI ACR TRR TAI GGI GC) were synthesized (H=A, C, or T, R=G or A, Y=T or C, I=inosine). Using a rhesus brain cDNA library (Clontech, Palo Alto, Calif.) as a template, PCR was carried out with the primers and the products were cloned into a pCR2.1-TOPO vector (Invitrogen, Carlsbad, Calif.). Fifteen clones were randomly picked up and sequenced with M13 forward and reverse primers by a dye-terminator method using ABI 377 sequencer (PE Biosystems, Foster City, Calif.). As a result, a partial sequence of rhesus MCH-2R cDNA was obtained.

To obtain the 5'- and 3'-end sequences, poly(A)+ RNAs were prepared from a rhesus whole brain using an Isogen reagent (Nippon Gene, Tokyo, Japan) and the cDNAs were generated by GeneRacer kit (Invitrogen), according to the manufacture's instructions. Four primers, mMCH2R-1 SEQ. ID. NO. 18 (AGACCATCCGGAT-CAATTTGGGCCT), mMCH2R-2;
SEQ. ID. NO. 19 (CCACCAGCACCAGCAC-CATCTTTGT), mMCH2R-3;
SEQ. ID. NO. 20 (TGGCATTGCCTGTCTGGATC-TACTCG) and mMCH2R-4; and,
SEQ. ID. NO. 21 (GGTACGCTGGGATTGCAA-CATCTGG) were designed and synthesized based on the above partial sequence. Employing the rhesus brain cDNAs, PCR-based RACE reactions were first carried out with mMCH2-1+GeneRacer 3' Primer (GCTGTCAAC-GATACGCTACGTAACG, SEQ. ID. NO. 22), and mMCH2R-2+GeneRacer 5'Primer (CGACTGGAGCAC-GAGGACACTGA, SEQ. ID. NO. 23). The PCR products from these reactions (primary reactions) were used as templates to carry out secondary PCR reactions using primers nested within the primary reactions, i.e., mMCH2R-3 (inside of mMCH2R-1)+GeneRacer 3' Nested Primer (CGCTACGTAACGGCATGACAGTG, SEQ. ID. NO. 24) for templates from mMCH2R-1-containing primary reactions, and mMCH2R4 (inside of mMCH2R-2)+GeneRacer 5'Nested Primer (GGACACT-GACATGGACTGAAGGAGTA, SEQ. ID. NO. 25) for templates from mMCH2R-2-containing primary reactions. The amplified products were cloned and sequenced as mentioned above. All nucleotide sequence data were analyzed and assembled using software Sequencher (Gene Codes, Ann Arbor, Mich.), resulting in the identification of an open reading frame of 1023 nucleotides encoding a polypeptide of 340 amino acids and a stop codon. The cDNA containing the entire ORF sequence was cloned by PCR using the rhesus brain cDNAs.

Example 2

Transient Expression of Rhesus Monkey MCH-2R

The entire coding sequence of rhesus MCH-2R was cloned into BamHI-NotI site of pEF1/V5-His C plasmid vector (Invitrogen). The resultant construct was transfected into HEK293T cells using LipofectAmine PLUS (Life Technologies, Rockville, Md.) according to the manufacture's instructions. Human embryonic kidney cells constitutively expressing SV40 large T antigen (HEK-293T) were maintained in Dulbecco's modified Eagle medium (Life Technologies) supplemented with 10% fetal bovine serum, 100 units/ml penicillin-G and 100 μg/ml streptomycin at 37° C. with 5% $CO_2$ in a humidified atmosphere.

The intracellular calcium ion concentration ($[Ca^{2+}]_i$) was measured fluorometrically using a $Ca^{2+}$-sensitive fluorescent dye, fura-2. HEK293T cells transiently transfected with pEF1/V5-HisC plasmid vector harboring rhesus MCH-2R cDNA were harvested by phosphate-buffered saline containing 2 mM EDTA 48 hours after transfection, and washed once with the assay buffer (Hanks' balanced salt solution containing 20 mM HEPES and 0.1% BSA, pH 7.4). The cells were suspended with the buffer containing 2 μM fura-2 acetoxymethylester (Dojin, Kumamoto, Japan) into the cell density of $1.0×10^7$ cells/ml and incubated at 37° C. for 60 minutes with gently shaking. The fura-2-loaded cells were washed twice with the buffer and re-suspended with the buffer to $1.0×10^6$ cells/ml. 0.5 ml of the resultant suspension was stirred continuously at 37° C. in a glass cuvette during the measurement. Two point five microliters of dimethyl sulfoxide (DMSO) solution of MCH (Peptide Institute, Osaka, Japan) or [$Phe^{13}$, $Tyr^{19}$]-MCH (Bachem, Bubendorf, Switzerland) was added into the cell suspension, and fluorescent intensity at an emission wavelength of 500 nm and excitation wavelengths of 340 and 380 nm was monitored with a CAF-110 intracellular ion analyzer (JASCO, Tokyo, Japan). Data were analyzed using the software GraphPad Prism Version 3.0 (GraphPad Software, Inc., San Diego, Calif., USA).

As shown in FIG. 3, both MCH and [$Phe^{13}$, $Tyr^{19}$]-MCH dose-dependently caused an increase in intracellular calcium levels in the HEK293T cells transiently expressing rhesus MCH-2R with potent efficacy ($EC_{50}$ of MCH and [$Phe^{13}$, Tyr$^{19}$]-MCH were calculated as 24 and 49 nM, respectively), but failed to induce a detectable [Ca$^{2+}$]$_i$ increase in the non-transfected cells (data not shown). These results confirm that the rhesus MCH-2R sequence encodes an active MCH receptor.

Example 3

MCH Binding to Rhesus Monkey MCH-2R

HEK293T cells were seeded into 24-well culture plates coated with poly-D-Lys at 1×10$^5$ cells/well and were cultured over-night. The adherent cells were transfected with pEF1/V5-HisC/rhesus MCH-2R plasmid (see Example 2). Forty-eight hours after transfection, the transfected monolayer cells were rinsed with the assay buffer (Hanks' balanced salt solution containing 20 mM HEPES, 0.2% BSA and 100 µg/ml bacitracin, pH 7.4). The cells were then incubated in 250 µl/well of the same buffer with [$^{125}$I]-MCH (100 pM, NEN Life Science Products, Boston, Mass.) or [$^{125}$I]-[Phe$^{13}$, Tyr$^{19}$]-MCH (100 pM, NEN Life Science Products) for 30 minutes at 37° C. After the incubation, the cells were washed three times with the ice cold assay buffer and lysed with 500 µl/well of 2 M NaOH. The lysates were transferred into test tubes and the cell-bound radioactivity was measured by a COBLA Quantum γ-counter (Packard Instrument, Meriden, Conn.). Nonspecific binding was defined in the presence of 1 µM cold MCH or [Phe$^{13}$, Tyr$^{19}$]-MCH for the corresponding radio ligands.

[$^{125}$I]-MCH and [$^{125}$I]-[Phe$^{13}$, Tyr$^{19}$]-MCH bound to the HEK293T cells expressing rhesus MCH-2R with good windows. Specific binding was not observed into mock transfected cells (Table 1).

TABLE 1

|  | [$^{125}$I]-MCH binding (cpm) | | [$^{125}$I]-[Phe$^{13}$, Tyr$^{19}$]-MCH binding (cpm) | |
| --- | --- | --- | --- | --- |
|  | Total binding | Nonspecific binding | Total binding | Nonspecific binding |
| rhesus | 2610.8 | 203.5 | 18749.0 | 717.0 |
| MCH-2R | 2299.4 | 532.1 | 17985.4 | 598.0 |
|  | 2475.8 | 268.2 | 18031.2 | 567.4 |
| Mock | 209.9 | 172.0 | 708.9 | 539.7 |
|  | 215.8 | 180.9 | 663.3 | 537.7 |
|  | 239.8 | 184.1 | 771.5 | 557.8 |

HEK293T cells transfected with pEF1/V5-HisC/MCH-2R plasmid were harvested by phosphate-buffered saline containing 2 mM EDTA 48 hours after transfection, and washed once with the assay buffer (Hanks' balanced salt solution containing 20 mM HEPES, 0.2% BSA and 100 µg/ml bacitracin, pH 7.4). The cells (4×10$^5$ cells/tube) were then incubated in 250 µl/tube of the same buffer with 100 pM [$^{125}$I]-[Phe$^{13}$, Tyr$^{19}$]-MCH for 30 minutes at 37° C. After the incubation, bound and free [$^{125}$I]-[Phe$^{13}$, Tyr$^{19}$]-MCH were separated by filtration using a Unifilter GF/B glass filter (Packard Instrument) presoaked with 0.3% polyethylenimine. The remaining radio activity on the filter was quantitated using a TopCount HTS (Packard instrument) with a Microscint 0 scintillation cocktail (Packard instrument). Specific binding was defined as the difference between total binding and nonspecific binding in the presence of 1 µM cold [Phe$^{13}$, Tyr$^{19}$]-MCH. Data were analyzed using GraphPad Prism Version 3.0.

Figure 4:
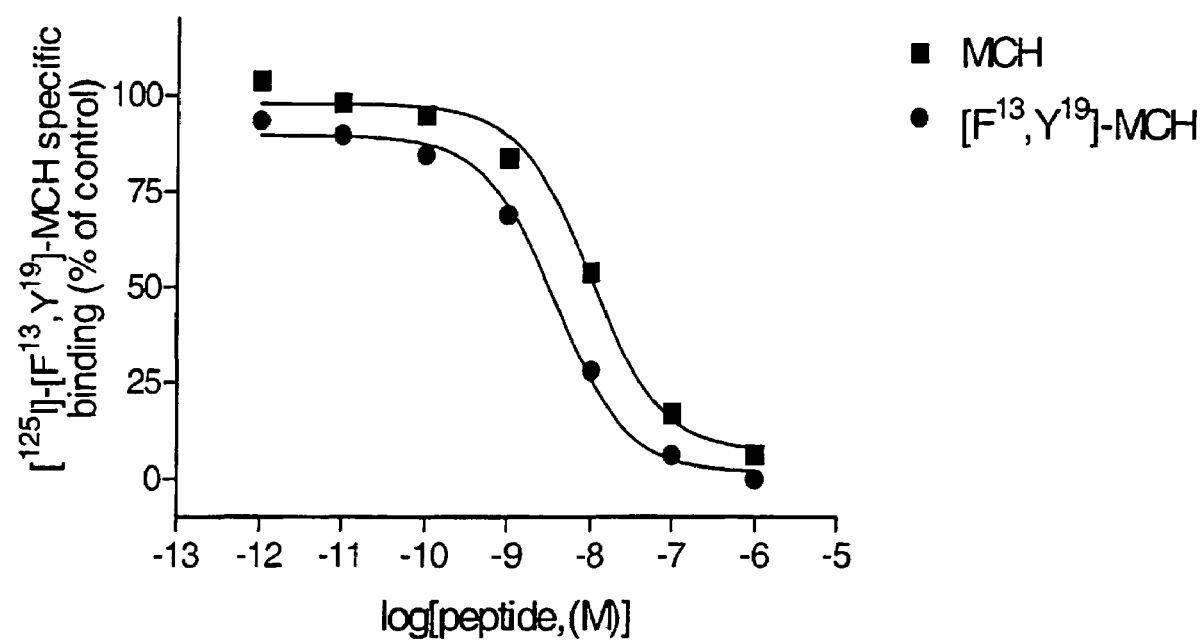
FIG. 4 illustrates the ability of MCH and [Phe$^{13}$, Tyr$^{19}$]-MCH to dose-dependently inhibit [$^{125}$I]-[Phe$^{13}$, Tyr$^{19}$]-MCH binding to the rhesus MCH-2R expressed on HEK293T cells.

As shown in FIG. 4, cold MCH and [Phe$^{13}$, Tyr$^{19}$]-MCH dose-dependently inhibited the [$^{125}$I]-[Phe$^{13}$, Tyr$^{19}$]-MCH binding to the rhesus MCH-2R expressed on HEK293T cells. IC$_{50}$ values of MCH and [Phe$^{13}$, Tyr$^{19}$]-MCH in this experiment were calculated as 9.9 and 3.8 nM, respectively.

Example 4

Cloning Dog and Ferret MCH-2R

Genomic MCH-2R was found to be provided for by five exons spanning more than 100 kB. The first part of the cloning involved PCR of fragments of exons 1, 2 and 3 from genomic DNA of various species by designing primers against human MCH-2R sequence.

The Exon primers were as follows:

Exon2 forward primer at bp 199 of human MCH-2R:
SEQ. ID. NO. 26 GTCCCTGACATCTATATCTGCAACC;
Exon2 reverse primer at bp392 of human MCH-2R:
SEQ. ID. NO. 27 CTGTCCACACTCATTACAGTCATGATG;
Exon3 forward primer at bp 393 of human MCH-2R:
SEQ. ID. NO. 28 GTACTTTGCCCTCGTCCAACC;
Exon3 reverse primer at bp 587 of human MCH-2R:
SEQ. ID. NO. 29 CAGAGTACATCGTCAGGGGATG;
Exon 1 forward primer at bp 1 of human MCH-2R:
SEQ. ID. NO. 30 ATGAATCCATTTCATGCATCTTGTTGGACC; and,
Exon1 reverse primer at bp182 of human MCH-2R:
SEQ. ID. NO. 31 CTTATTATAGTGAATACAATGAGGATGTTGCC.

For cloning dog MCH-2R a Catahula Leopard dog brain was procured from Pelfreeze. The whole brain was ground up to a fine powder in liquid nitrogen using a mortar and pestle. PolyA RNA was prepared using the Poly A Pure kit (Ambion) per manufacturer's instructions. First strand cDNA was transcribed off the mRNA using Superscipt RT II kit (BRL).

For cloning ferret MCH-2R, a whole ferret brain was ground up to a fine powder in liquid nitrogen using a mortar and pestle. PolyA RNA was prepared using the Poly A Pure kit (Ambion) per manufacturer's instructions. First strand cDNA was transcribed off the mRNA using Superscipt RT II kit (BRL).

Dog and ferret MCH-2R specific forward primer at exon1 was 5'-CCTTCTATGATTGGGATTATCTGTTCAATG-3' (SEQ. ID. NO. 32) (same primer for both). For both dog and ferret, the same reverse primer in mid-exon5 was used: 5'-GTTAATGCTGCTGCTGGCATAGC-3' (SEQ. ID. NO. 33).

The reverse primer falls within a region of 100% homology between human MCH-1R and human MCH-2R. The expectation was that it would be perfectly conserved between the ferret and dog MCH-2R. It turns out the assumption was correct when dog and ferret 2R sequence was determined at that position in subsequent experiments.

RT-PCR was performed out of whole brain cDNA for dog and ferret and near complete clones were obtained. The missing dog exon1 and ferret exon1 sequence was filled in with the original PCR sequence determined from genomic PCR described above.

The 3' end of dog mCH2R was determined by subcloning of exon5 fragment of a dog BAC clone. The human primer sequence at the 5' end of the gene was converted to dog MCH2R sequence after the dog BAC exon1 fragment was cloned. Three way overlapping PCR was performed to splice together the three pieces of the dog to generate an open-reading-frame (ORF).

Exon 5 was completed by PCR out of ferret genomic DNA using a ferret MCH-2R specific forward primer and a human MCH-2R reverse primer (last 30 bp of human MCH2R sequence). The ferret MCH-2R exon5 forward primer has the following sequence: 5'-GATGGAGCAGC-CCACACTGGCCTTC-3' (SEQ. ID. NO. 34).

Ferret MCH-2R ORF was also generated by three way overlapping PCR. There was no BAC subcloning, so the very 5' and 3' ends of ferret MCH-2R (first and last 10 amino acids) are human ends.

Example 5

Ferret MCH-2R Binding and Activity Data

This example illustrates the ability of the ferret MCH-2R to bind MCH and to be activated by MCH.

Radioligand Binding Assays

Membrane binding assays were performed on transiently-transfected COS-7 cells using human or ferret MCH-2R in the plasmid vector pCI-neo (Promega, Madison, Wis.), COS-7 cells were cultured in Dulbecco's modified Eagle medium (Gibco BRL, Rockville, Md.) with 10% heat inactivated fetal calf serum.

A suspension of $7\times10^6$ COS-7 cells were transfected with 20 µg of pCI-neo/MCH-2R plasmid by electroporation. (Strader, et al., 1987. *Proc. Natl. Acad. Sci. USA* 84, 4384–4388). Cells were harvested after 60–72 hours. Membranes were prepared from transient and stable transfectants by hypotonic lysis, frozen in liquid nitrogen, and stored at –80° C. (MacNeil, et al., 1994. *Biochem. Biophys. Res. Commun.* 198, 328–334.)

A binding assay was set up in 96 well plates. Total volume per binding assay point was 200 µL. Binding conditions were 50 mM Tris pH 7.4, 10 mM $MgCl_2$, 2 mM EDTA 200 µg/mL bacitracin, 1 µM phosphoramidon, 2.5 to 5 µg protein, with and without 10 µM MCH unlabeled peptide as a competitor. Dose response curves were from 10 µM in 5 fold or 3-fold dilution series for 11 points. The mixture was shaken for 5 minutes on a platform shaker, and incubated at room temperature for 1 hour. Filter plates were presoaked in 1% PEI. The binding reaction was harvested onto filters using Packard Filtermate harvester (Meriden, Conn.). The filters were then washed in 50 mM Tris pH 7.4, 10 mM $MgCl_2$, 2 mM EDTA, 0.04% Tween 20, 6–8 times per plate. The plates were dried for 20 minutes at 55° C. or overnight at room temperature. 30 µL microscintillant was added per well and counted for 1.5–3 minutes in inverted format on Packard TopCount. $IC_{50}$ calculations were performed using Prism 3.0 (GraphPad Software, San Diego, Calif.).

Aequorin Bioluminescence Functional Assay

The aequorin bioluminescence assay is a reliable test for identifying G-protein-coupled receptors which couple through the G protein subunit family consisting of Gq and G11 which leads to the activation of phospholipase C, mobilization of intracellular calcium, and activation of protein kinase C. (Ungrin, et al., *Anal. Biochem.* 1999. 272: 34–42.)

For expression studies, HEK-293 cells stably expressing the aequorin reporter protein were transiently transfected with MCH-2R human or ferret expression plasmid or stable cell lines were derived (human MCH-2R). The assay was performed using a Luminoscan RT luminometer (Labsystems Inc., Gaithersburg, Md.).

293AEQ17/Aequorin cells (Button, et al., 1993. *Cell Calcium* 14, 663–671), were cultured for 72 hours and the apo-aequorin in the cells was charged for 1 hour with coelenterazine (10 µM) under reducing conditions (300 µM reduced glutathione) in ECB buffer (140 mM NaCl, 20 mM KCl, 20 mM HEPES-NaOH, pH 7.4, 5 mM glucose, 1 mM $MgCl_2$, 1 mM $CaCl_2$, 0.1 mg/mL bovine serum albumin). The cells were harvested, washed once in ECB medium, and resuspended to 500,000 cells/mL. 100 µL of cell suspension (corresponding to $5\times10^4$ cells) was then injected into the test plate containing ligands, and the integrated light emission was recorded over 30 seconds, in 0.5-second units. 20 µL of lysis buffer (0.1% final Triton X-100 concentration) was then injected and the integrated light emission recorded over 10 seconds, in 0.5-second units.

The "fractional response" values for each well were calculated by taking the ratio of the integrated response to the initial challenge to the total integrated luminescence including the Triton X-100 lysis response. The functional $EC_{50}$ values were measured in three separate assays.

Binding and functional data for human and ferret MCH-2R is provided in Table 2.

TABLE 2

| Species | Binding (IC50, nM) MCH | Function (EC50, nM) MCH |
|---|---|---|
| Human | 10 | 43 |
| Ferret | 55 | 69 |

Other embodiments are within the following claims. While several embodiments have been shown and described, various modifications may be made without departing from the spirit and scope of the present invention.

What is claimed is:

1. A purified polypeptide comprising an amino acid SEQ ID NO: 9.

2. The polypeptide of claim 1, wherein said polypeptide consists of an MCH-2R dog, ferret, or rhesus sequence comprising SEQ ID NO: 9.

3. The polypeptide of claim 1, wherein said polypeptide comprises a sequence selected from the group consisting of SEQ ID NO: 1, SEQ ID NO: 2, and SEQ ID NO: 3.

4. The polypeptide of claim 3, wherein said polypeptide consists of SEQ ID NO: 1.

5. The polypeptide of claim 3, wherein said polypeptide consists of SEQ ID NO: 2.

6. The polypeptide of claim 3, wherein said polypeptide consists of SEQ ID NO: 3.

7. A purified nucleic acid comprising a nucleotide sequence selected from the group consisting of: SEQ ID NO: 13 and the complement of SEQ ID NO: 13.

8. A method of measuring the ability of a compound to affect MCH-2R activity comprising the steps of:
   a) contacting a recombinant cell with said compound, wherein said recombinant cell comprises a recombinant nucleic acid expressing a functional MCH-2R that comprises the amino acid sequence of either SEQ ID NO: 1 SEQ ID NO: 2 or SEQ ID NO: 3; and
   b) measuring MCH-2R activity.

9. The method of claim 8, wherein said method further comprises the use of an MCH-2R agonist.

10. The method of claim 8, wherein said amino acid sequence is SEQ ID NO: 3.

11. A recombinant nucleic acid comprising a nucleotide sequence encoding the amino acid sequence of SEQ ID NO: 9.

12. The recombinant nucleic acid of claim 11, wherein said nucleotide encodes the sequence of either SEQ ID NO: 1, SEQ ID NO: 2, or SEQ ID NO: 3.

13. The recombinant nucleic acid of claim 12, wherein said recombinant nucleic acid is an expression vector.

14. The recombinant nucleic acid of claim 11, wherein said nucleotide sequence encodes SEQ ID NO: 3.

15. The recombinant nucleic acid of claim 11, wherein said nucleotide sequence is selected from the group consisting of: SEQ ID NO: 5, SEQ ID NO: 6, and SEQ ID NO: 7.

16. The recombinant nucleic acid of claim 15, wherein said nucleotide sequence is NO: 7.

17. A recombinant cell comprising the expression vector of claim 12, wherein said nucleotide sequence is functionally coupled to a promoter recognized by said cell.

18. A method of preparing a MCH-2R polypeptide comprising the step of growing the recombinant cell of claim 17 under conditions wherein said polypeptide is expressed from said expression vector.

* * * * *

SEQUENCE LISTING

<160> NUMBER OF SEQ ID NOS: 34

<210> SEQ ID NO 1
<211> LENGTH: 330
<212> TYPE: PRT
<213> ORGANISM: Dog

<400> SEQUENCE: 1

Met Tyr Ser Leu His Ser Ser Cys Trp Asn Thr Ser Ala Glu Pro Leu
1               5                   10                  15

Asn Lys Ser Cys Asn Lys Glu Phe Ala Tyr His Thr Leu Ser Ile Leu

-continued

```
                    20                  25                  30
Asp Thr Ile Arg Leu Pro Ser Met Ile Gly Ile Cys Ser Met Gly
             35                  40                  45
Leu Val Gly Asn Ile Leu Ile Val Phe Thr Ile Ile Arg Ser Arg Lys
 50                  55                  60
Lys Thr Ile Pro Asp Ile Tyr Ile Cys Asn Leu Ala Val Ala Asp Leu
 65                  70                  75                  80
Val His Ile Ile Gly Met Pro Phe Leu Ile His Gln Trp Ala Arg Gly
                 85                  90                  95
Gly Glu Trp Val Phe Gly Gly Pro Leu Cys Thr Ile Thr Ser Leu
                100                 105                 110
Asp Thr Cys Asn Gln Phe Ala Cys Ser Ala Ile Met Thr Val Met Ser
                115                 120                 125
Ile Asp Arg Tyr Leu Ala Leu Val Gln Pro Phe Arg Leu Thr Ser Trp
130                 135                 140
Arg Thr Arg Tyr Lys Thr Ile Arg Ile Asn Leu Gly Leu Trp Ala Ala
145                 150                 155                 160
Ser Phe Ile Leu Ala Leu Pro Val Trp Val Tyr Ser Lys Val Ile Lys
                165                 170                 175
Phe Lys Asp Gly Val Glu Ser Cys Ala Phe Asp Leu Thr Ser Pro Asp
                180                 185                 190
Asp Val Leu Arg Tyr Thr Leu Tyr Leu Thr Ile Thr Thr Phe Phe
                195                 200                 205
Pro Leu Pro Leu Ile Leu Val Cys Tyr Ile Leu Ile Leu Cys Tyr Thr
                210                 215                 220
Trp Glu Met Tyr Gln Gln Asn Lys Asp Ala Arg Cys Tyr Asn Pro Ser
225                 230                 235                 240
Val Pro Lys Glu Arg Val Met Lys Leu Thr Lys Met Val Leu Val Leu
                245                 250                 255
Val Ala Val Phe Ile Leu Ser Ala Ala Pro Tyr His Val Ile Gln Leu
                260                 265                 270
Val Asn Leu Lys Met Gln Gln Pro Thr Leu Ala Phe His Val Gly Tyr
                275                 280                 285
Tyr Leu Ser Ile Cys Phe Ser Tyr Ala Ser Ser Ser Ile Asn Pro Phe
                290                 295                 300
Leu Tyr Ile Met Leu Ser Gly Asn Phe Arg Lys Arg Leu Pro Gln Val
305                 310                 315                 320
Gln Arg Arg Val Thr Glu Lys Ser Thr Ile
                325                 330

<210> SEQ ID NO 2
<211> LENGTH: 340
<212> TYPE: PRT
<213> ORGANISM: Ferret

<400> SEQUENCE: 2

Met Asn Pro Phe His Ala Ser Cys Trp Asn Thr Ser Ala Glu Leu Leu
  1               5                  10                  15
Asn Lys Ser Cys Asn Lys Glu Ser Ala Tyr Gln Thr Leu Arg Ile Val
                 20                  25                  30
Asp Thr Ile Ile Leu Pro Ser Met Ile Gly Ile Ile Cys Ser Met Gly
             35                  40                  45
Leu Val Gly Asn Val Leu Ile Val Phe Thr Ile Ile Arg Ser Arg Lys
 50                  55                  60
```

```
Lys Thr Ile Pro Asp Ile Tyr Ile Cys Asn Leu Ala Val Ala Asp Leu
 65                  70                  75                  80

Val His Ile Ile Gly Met Pro Phe Leu Ile His Gln Trp Ala Arg Gly
                 85                  90                  95

Gly Glu Trp Val Phe Gly Gly Pro Leu Cys Thr Ile Ile Thr Ser Leu
            100                 105                 110

Asp Thr Cys Asn Gln Phe Ala Cys Ser Ala Ile Met Thr Val Met Ser
        115                 120                 125

Val Asp Arg Tyr Leu Ala Leu Val Gln Pro Phe Arg Leu Thr Ser Trp
    130                 135                 140

Arg Thr Arg Tyr Lys Thr Ile Arg Ile Asn Leu Gly Leu Trp Ala Ala
145                 150                 155                 160

Ser Phe Ile Leu Ala Leu Pro Val Trp Val Tyr Ser Lys Val Ile Lys
                165                 170                 175

Phe Lys Asp Gly Val Glu Ser Cys Ala Phe Asp Leu Thr Ser Pro Asp
            180                 185                 190

Asp Val Leu Arg Tyr Thr Leu Tyr Leu Thr Ile Thr Thr Phe Phe Phe
        195                 200                 205

Pro Leu Pro Leu Ile Leu Val Cys Tyr Ile Leu Ile Leu Cys Tyr Thr
    210                 215                 220

Trp Glu Met Tyr Gln Gln Asn Lys Asp Ala Arg Cys Tyr Asn Pro Ser
225                 230                 235                 240

Val Pro Lys Glu Arg Val Met Lys Leu Thr Lys Met Val Leu Val Leu
                245                 250                 255

Val Ala Val Phe Ile Leu Ser Ala Ala Pro Tyr His Val Ile Gln Leu
            260                 265                 270

Val Asn Leu Gln Met Glu Gln Pro Thr Leu Ala Phe His Val Gly Tyr
        275                 280                 285

Tyr Leu Ser Ile Cys Phe Ser Tyr Ala Ser Ser Ser Ile Asn Pro Phe
    290                 295                 300

Leu Tyr Ile Met Leu Ser Gly Asn Phe Arg Lys Arg Leu Pro Gln Val
305                 310                 315                 320

Gln Arg Arg Val Thr Glu Arg Glu Ile Asn Asn Met Gly Asn Thr Leu
                325                 330                 335

Lys Ser His Phe
            340

<210> SEQ ID NO 3
<211> LENGTH: 340
<212> TYPE: PRT
<213> ORGANISM: Rhesus Monkey

<400> SEQUENCE: 3

Met Asn Pro Phe His Ser Ser Cys Trp Asn Thr Ser Ala Glu Leu Ser
  1               5                  10                  15

Asn Lys Ser Trp Asn Lys Glu Phe Ala Tyr Gln Thr Ala Ser Val Val
             20                  25                  30

Asp Thr Val Ile Leu Pro Ser Met Ile Gly Ile Ile Cys Ser Thr Gly
         35                  40                  45

Leu Val Gly Asn Ile Leu Ile Val Phe Thr Ile Ile Arg Ser Arg Lys
     50                  55                  60

Lys Thr Val Pro Asp Ile Tyr Ile Cys Asn Leu Ala Val Ala Asp Leu
 65                  70                  75                  80

Val His Ile Ile Gly Met Pro Phe Leu Ile His Gln Trp Ala Arg Gly
                 85                  90                  95
```

-continued

```
Gly Glu Trp Val Phe Gly Gly Pro Leu Cys Thr Ile Ile Thr Ser Leu
            100                 105                 110

Asp Thr Cys Asn Gln Phe Ala Cys Ser Ala Ile Met Thr Val Met Ser
            115                 120                 125

Val Asp Arg Tyr Phe Ala Leu Val Gln Pro Phe Arg Leu Thr Ser Trp
            130                 135                 140

Arg Thr Arg Tyr Lys Thr Ile Arg Ile Asn Leu Gly Leu Trp Ala Ala
145                 150                 155                 160

Ser Phe Val Leu Ala Leu Pro Val Trp Ile Tyr Ser Lys Val Ile Lys
            165                 170                 175

Phe Lys Asp Gly Val Glu Ser Cys Ala Phe Asp Leu Thr Ser Pro Asp
            180                 185                 190

Asp Val Leu Trp Tyr Thr Leu Tyr Leu Thr Ile Thr Thr Phe Phe Phe
            195                 200                 205

Pro Leu Pro Leu Ile Leu Val Cys Tyr Ile Leu Ile Leu Cys Tyr Thr
            210                 215                 220

Trp Glu Met Tyr Gln Gln Asn Lys Asp Ala Arg Cys Cys Asn Pro Ser
225                 230                 235                 240

Val Pro Lys Gln Arg Val Met Lys Leu Thr Lys Met Val Leu Val Leu
            245                 250                 255

Val Ala Val Phe Ile Leu Ser Ala Ala Pro Tyr His Val Ile Gln Leu
            260                 265                 270

Val Asn Leu Gln Met Glu Gln Pro Thr Leu Ala Phe Tyr Val Gly Tyr
            275                 280                 285

Tyr Leu Ser Ile Cys Leu Ser Tyr Ala Ser Ser Ile Asn Pro Phe
            290                 295                 300

Leu Tyr Ile Leu Leu Ser Gly Asn Phe Gln Lys Arg Leu Pro Gln Ile
305                 310                 315                 320

Gln Arg Arg Val Thr Asp Lys Glu Ile Lys Asn Met Gly Asn Thr Leu
            325                 330                 335

Lys Ser His Phe
            340

<210> SEQ ID NO 4
<211> LENGTH: 340
<212> TYPE: PRT
<213> ORGANISM: Human

<400> SEQUENCE: 4

Met Asn Pro Phe His Ala Ser Cys Trp Asn Thr Ser Ala Glu Leu Leu
1               5                   10                  15

Asn Lys Ser Trp Asn Lys Glu Phe Ala Tyr Gln Thr Ala Ser Val Val
            20                  25                  30

Asp Thr Val Ile Leu Pro Ser Met Ile Gly Ile Ile Cys Ser Thr Gly
            35                  40                  45

Leu Val Gly Asn Ile Leu Ile Val Phe Thr Ile Ile Arg Ser Arg Lys
50                  55                  60

Lys Thr Val Pro Asp Ile Tyr Ile Cys Asn Leu Ala Val Ala Asp Leu
65                  70                  75                  80

Val His Ile Val Gly Met Pro Phe Leu Ile His Gln Trp Ala Arg Gly
            85                  90                  95

Gly Glu Trp Val Phe Gly Gly Pro Leu Cys Thr Ile Ile Thr Ser Leu
            100                 105                 110

Asp Thr Cys Asn Gln Phe Ala Cys Ser Ala Ile Met Thr Val Met Ser
            115                 120                 125
```

```
            115                 120                 125
Val Asp Arg Tyr Phe Ala Leu Val Gln Pro Phe Arg Leu Thr Arg Trp
    130                 135                 140

Arg Thr Arg Tyr Lys Thr Ile Arg Ile Asn Leu Gly Leu Trp Ala Ala
145                 150                 155                 160

Ser Phe Ile Leu Ala Leu Pro Val Trp Val Tyr Ser Lys Val Ile Lys
                165                 170                 175

Phe Lys Asp Gly Val Glu Ser Cys Ala Phe Asp Leu Thr Ser Pro Asp
            180                 185                 190

Asp Val Leu Trp Tyr Thr Leu Tyr Leu Thr Ile Thr Thr Phe Phe Phe
        195                 200                 205

Pro Leu Pro Leu Ile Leu Val Cys Tyr Ile Leu Ile Leu Cys Tyr Thr
    210                 215                 220

Trp Glu Met Tyr Gln Gln Asn Lys Asp Ala Arg Cys Cys Asn Pro Ser
225                 230                 235                 240

Val Pro Lys Gln Arg Val Met Lys Leu Thr Lys Met Val Leu Val Leu
                245                 250                 255

Val Val Val Phe Ile Leu Ser Ala Ala Pro Tyr His Val Ile Gln Leu
            260                 265                 270

Val Asn Leu Gln Met Glu Gln Pro Thr Leu Ala Phe Tyr Val Gly Tyr
        275                 280                 285

Tyr Leu Ser Ile Cys Leu Ser Tyr Ala Ser Ser Ser Ile Asn Pro Phe
    290                 295                 300

Leu Tyr Ile Leu Leu Ser Gly Asn Phe Gln Lys Arg Leu Pro Gln Ile
305                 310                 315                 320

Gln Arg Arg Ala Thr Glu Lys Glu Ile Asn Asn Met Gly Asn Thr Leu
                325                 330                 335

Lys Ser His Phe
            340

<210> SEQ ID NO 5
<211> LENGTH: 993
<212> TYPE: DNA
<213> ORGANISM: Dog

<400> SEQUENCE: 5
atgtattcac ttcactcatc ctgttggaac acctctgctg aacctttgaa caaatcctgc      60
aataaagagt tgcttatca caccctcagc atttagata cartcaggct tccttctatg      120
attgggatta tctgttcaat ggggctagtt ggcaacatcc tcattgtatt cactataata      180
aggtccagga aaaaaccat tcctgacatt tatatctgca acctggctgt ggctgatctg      240
gtccacatca ttggaatgcc atttcttatt catcagtggg cccggggagg agagtgggtg      300 tttgggggc ccctctgcac cattatcaca tccctggata cctgcaacca gtttgcctgt      360
agtgccatca tgactgtgat gagtatagac aggtacttgg ctctcgtcca accatttcga      420
cttacaagtt ggagaacgag gtacaagacc atccgcatca atttgggcct tgggcagct      480 tccttcattc tggcgctgcc tgtctgggtc tactcgaagg tcatcaaatt taagacggc      540 gtggagagtt gtgcttttga tttaacatcc cctgacgatg tactccggta cactttat       600 ttgacgataa caactttttt tttccctttg cctttgattt tggtgtgcta tattttaatt     660
ttatgctata cttgggagat gtatcaacag aataaagatg caagatgtta caatcccagt      720
gttccaaaag agagagtgat gaagctgaca aagatggtgc tggtgctggt ggcggtcttt      780
atcctaagtg ctgcccccta ccacgtgata caactggtga acttaaagat gcagcagccc      840
```

```
acactggcct tccatgtagg ctattatctc tccatctgtt tcagctatgc cagcagcagc    900
attaaccctt tcctctacat catgctgagt ggaaatttcc ggaaacgcct acctcaagta    960
caaaggagag tgactgagaa atcaacaata tag                                 993
```

<210> SEQ ID NO 6
<211> LENGTH: 1023
<212> TYPE: DNA
<213> ORGANISM: Ferret

<400> SEQUENCE: 6

```
atgaatccat tcatgcatc ttgttggaac acctctgctg aacttttaaa caaatcctgc      60
aataaagaat ctgcttatca aaccctcaga attgtggata caatcatcct tccttctatg    120
attgggatta tctgttcaat ggggctggtt ggcaatgtcc tcattgtatt cactataata    180
aggtccagga aaaaaaccat tcctgacatt tatatctgca acctggctgt agctgatctg    240
gttcacatca ttggaatgcc ttttcttatt catcaatggg cccggggagg agagtgggtg    300
tttgggggc ccctctgcac cattatcacg tcgctggata cctgcaacca gtttgcttgt    360
agcgccatca tgactgtgat gagtgtggac aggtacttgg ctctcgtcca accatttcga    420
cttacaagtt ggagaacgag gtacaagacc atccgcatca atttgggcct ttgggcagct    480
tccttcattc tggcgttgcc tgtctgggtc tactcgaagg tcatcaaatt taaagacggc    540
gtggagagtt gtgcttttga tttaacatcc cctgacgatg tactccggta tacactttat    600
ctgacgataa caacttttttt tttttcctttg cctttgattt tggtgtgcta tattttaatt    660
ttatgctata cttgggagat gtatcaacag aataaggatg ccagatgtta caaccccagt    720
gttccaaaag agagagtgat gaagctgaca agatggtgc tggtgttggt ggcagtcttt    780
atcctgagtg ctgcccccta ccatgtgata caactggtga atttacagat ggagcagccc    840
acactggcct tccatgtagg ctattatctc tccatctgtt tcagctatgc cagcagcagc    900
attaatcctt tcctctacat catgctgagt ggaaatttcc ggaaacgcct gcctcaagtg    960
caaagaagag tgactgagag ggaaatcaac aatatgggaa acactctgaa atcacacttt   1020
tag                                                                 1023
```

<210> SEQ ID NO 7
<211> LENGTH: 1023
<212> TYPE: DNA
<213> ORGANISM: Rhesus Monkey

<400> SEQUENCE: 7

```
atgaatccat tcactcatc ttgttggaac acctctgccg aactttcaaa caaatcctgg      60
aataaagagt ttgcttatca aactgccagt gttgtagata cagtcatcct cccttccatg    120
attgggatta tctgttcaac agggctggtt ggcaacatcc tcattgtatt cactataata    180
aggtccagaa aaaaaacagt ccctgacatc tatatctgca acctggctgt ggctgatttg    240
gtccacatca ttggaatgcc ttttcttatt caccagtggg cccgaggggg agagtggta    300
tttgggggc ctctctgcac catcatcaca tccctggata cttgtaacca atttgcctgt    360
agtgccatca tgactgtaat gagtgtggac aggtactttg ccctcgtcca accatttcga    420
ctgacaagtt ggagaacaag gtacaagacc atccggatca atttgggcct ttgggcagct    480
tcctttgtcc tggcattgcc tgtctggatc tactcgaagg tcatcaaatt taaagacggt    540
gtcgagagtt gtgcttttga tttgacatcc cctgacgatg tactctggta tacactttat    600
```

-continued

```
ttgacaataa caactttctt tttccctcta cccttgattt tggtgtgcta tattttaatt      660
ttatgctata cttgggagat gtatcaacag aataaggatg ccagatgttg caatcccagc      720
gtaccaaaac agagagtgat gaagttgaca aagatggtgc tggtgctggt ggcagtcttt      780
atcctaagtg ctgcccctta tcatgtgata caactggtga acttacagat ggaacagccc     840
acactggcct tctatgtggg ttattacctc tccatctgtc tcagctatgc cagcagcagc     900
attaaccctt ttctctacat cctgctgagt ggаааттттcс agaaacgtct gcctcaaatc   960
caaaggagag tgactgacaa ggaaatcaaa aatatgggaa acactctgaa atcacacttt    1020
tag                                                                 1023
```

<210> SEQ ID NO 8
<211> LENGTH: 1023
<212> TYPE: DNA
<213> ORGANISM: Human

<400> SEQUENCE: 8

```
atgaatccat tcatgcatc ttgttggaac acctctgctg aacttttaaa caaatcctgc       60
aataaagaat ctgcttatca aaccctcaga attgtggata caatcatcct tccttctatg    120
attgggatta tctgttcaat ggggctggtt ggcaatgtcc tcattgtatt cactataata    180
aggtccagga aaaaaaccat tcctgacatt tatatctgca acctggctgt agctgatctg    240
gttcacatca ttggaatgcc ttttcttatt catcaatggg cccggggagg agagtgggtg    300 tttgggggc ccctctgcac cattatcacg tcgctggata cctgcaacca gtttgcttgt    360
agcgccatca tgactgtgat gagtgtggac aggtacttgg ctctcgtcca accatttcga   420
cttacaagtt ggagaacgag gtacaagacc atccgcatca atttgggcct ttgggcagct    480
tccttcattc tggcgttgcc tgtctgggtc tactcgaagg tcatcaaatt taaagacggc    540
gtggagagtt gtgcttttga tttaacatcc cctgacgatg tactccggta tacactttat    600
ctgacgataa caactttttt ttttcctttg cctttgattt tggtgtgcta tattttaatt   660
ttatgctata cttgggagat gtatcaacag aataaggatg ccagatgtta caaccccagt   720
gttccaaaag agagagtgat gaagctgaca aagatggtgc tggtgttggt ggcagtcttt    780

atcctgagtg ctgcccccta ccatgtgata caactggtga atttacagat ggagcagccc   840
acactggcct tccatgtagg ctattatctc tccatctgtt tcagctatgc cagcagcagc    900

attaatcctt ccctctacat catgctgagt ggаааттттcc ggaaacgcct gcctcaagtg   960
caaagaagag tgactgagag ggaaatcaac aatatgggaa acactctgaa atcacacttt   1020
tag                                                                 1023
```

<210> SEQ ID NO 9
<211> LENGTH: 10
<212> TYPE: PRT
<213> ORGANISM: Artificial Sequence
<220> FEATURE:
<223> OTHER INFORMATION: MCH-2R polypeptide

<400> SEQUENCE: 9

Asp Leu Val His Ile Ile Gly Met Pro Phe
 1               5                  10

<210> SEQ ID NO 10
<211> LENGTH: 10
<212> TYPE: PRT
<213> ORGANISM: Artificial Sequence
<220> FEATURE:

<223> OTHER INFORMATION: MCH-2R polypeptide

<400> SEQUENCE: 10

Leu Thr Ser Trp Arg Thr Arg Tyr Lys Thr
1               5                   10

<210> SEQ ID NO 11
<211> LENGTH: 10
<212> TYPE: PRT
<213> ORGANISM: Artificial Sequence
<220> FEATURE:
<223> OTHER INFORMATION: MCH-2R polypeptide

<400> SEQUENCE: 11

Lys Met Val Leu Val Leu Val Ala Val Phe
1               5                   10

<210> SEQ ID NO 12
<211> LENGTH: 18
<212> TYPE: DNA
<213> ORGANISM: Artificial Sequence
<220> FEATURE:
<223> OTHER INFORMATION: MCH-2R polynucleotide

<400> SEQUENCE: 12
ctataataag gtccagaa                                                    18

<210> SEQ ID NO 13
<211> LENGTH: 17
<212> TYPE: DNA
<213> ORGANISM: Artificial Sequence
<220> FEATURE:
<223> OTHER INFORMATION: MCH-2R polynucleotide

<400> SEQUENCE: 13
cacatcattg gaatgcc                                                     17

<210> SEQ ID NO 14
<211> LENGTH: 14
<212> TYPE: DNA
<213> ORGANISM: Artificial Sequence
<220> FEATURE:
<223> OTHER INFORMATION: MCH-2R polynucleotide

<400> SEQUENCE: 14
acaagttgga gaac                                                        14

<210> SEQ ID NO 15
<211> LENGTH: 11
<212> TYPE: DNA
<213> ORGANISM: Artificial Sequence
<220> FEATURE:
<223> OTHER INFORMATION: MCH-2R polynucleotide

<400> SEQUENCE: 15
agagtgactg a                                                           11

<210> SEQ ID NO 16
<211> LENGTH: 23
<212> TYPE: DNA
<213> ORGANISM: Artificial Sequence
<220> FEATURE:
<223> OTHER INFORMATION: Oligonucleotide primerI
<220> FEATURE:
<221> NAME/KEY: modified_base
<222> LOCATION: (3)...(3)
<223> OTHER INFORMATION: n = I

```
<220> FEATURE:
<221> NAME/KEY: modified_base
<222> LOCATION: (9)...(9)
<223> OTHER INFORMATION: n = I
<220> FEATURE:
<221> NAME/KEY: modified_base
<222> LOCATION: (15)...(15)
<223> OTHER INFORMATION: n = I

<400> SEQUENCE: 16
ggnatgccnt tyhtnathca yca                                    23

<210> SEQ ID NO 17
<211> LENGTH: 23
<212> TYPE: DNA
<213> ORGANISM: Artificial Sequence
<220> FEATURE:
<223> OTHER INFORMATION: Oligonucleotide primer
<220> FEATURE:
<221> NAME/KEY: modified_base
<222> LOCATION: (6)...(6)
<223> OTHER INFORMATION: n = I
<220> FEATURE:
<221> NAME/KEY: modified_base
<222> LOCATION: (9)...(9)
<223> OTHER INFORMATION: n = I
<220> FEATURE:
<221> NAME/KEY: modified_base
<222> LOCATION: (18)...(18)
<223> OTHER INFORMATION: n = I
<220> FEATURE:
<221> NAME/KEY: modified_base
<222> LOCATION: (21)...(21)
<223> OTHER INFORMATION: n = I

<400> SEQUENCE: 17
arytgnadna crtrrtangg ngc                                    23

<210> SEQ ID NO 18
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 18
agaccatccg gatcaatttg ggcct                                  25

<210> SEQ ID NO 19
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 19
ccaccagcac cagcaccatc tttgt                                  25

<210> SEQ ID NO 20
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 20
tggcattgcc tgtctggatc tactcg                                 26

<210> SEQ ID NO 21
```

```
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 21
ggtacgctgg gattgcaaca tctgg                                          25

<210> SEQ ID NO 22
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 22
gctgtcaacg atacgctacg taacg                                          25

<210> SEQ ID NO 23
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 23
cgactggagc acgaggacac tga                                            23

<210> SEQ ID NO 24
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 24
cgctacgtaa cggcatgaca gtg                                            23

<210> SEQ ID NO 25
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 25
ggacactgac atggactgaa ggagta                                         26

<210> SEQ ID NO 26
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 26
gtccctgaca tctatatctg caacc                                          25

<210> SEQ ID NO 27
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 27
```

-continued ctgtccacac tcattacagt catgatg                                    27

<210> SEQ ID NO 28
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 28
gtactttgcc ctcgtccaac c                                          21

<210> SEQ ID NO 29
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 29
cagagtacat cgtcagggga tg                                         22

<210> SEQ ID NO 30
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 30
atgaatccat ttcatgcatc ttgttggacc                                 30

<210> SEQ ID NO 31
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 31
cttattatag tgaatacaat gaggatgttg cc                              32

<210> SEQ ID NO 32
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 32
ccttctatga ttgggattat ctgttcaatg                                 30

<210> SEQ ID NO 33
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 33
gttaatgctg ctgctggcat agc                                        23

<210> SEQ ID NO 34
<211> LENGTH: 25
<212> TYPE: DNA

-continued

```
<213> ORGANISM: Artificial Sequence
<220> FEATURE:
<223> OTHER INFORMATION: Oligonucleotide primer

<400> SEQUENCE: 34
gatggagcag cccacactgg ccttc                                              25
```